US007686763B2

(12) United States Patent
Vaezy et al.

(10) Patent No.: US 7,686,763 B2
(45) Date of Patent: Mar. 30, 2010

(54) USE OF CONTRAST AGENTS TO INCREASE THE EFFECTIVENESS OF HIGH INTENSITY FOCUSED ULTRASOUND THERAPY

(75) Inventors: Shahram Vaezy, Seattle, WA (US); Roy W. Martin, Anacortes, WA (US); Stephen J. Carter, La Conner, WA (US); Lawrence A. Crum, Bellevue, WA (US)

(73) Assignee: University of Washington, Seattle, WA (US)

( * ) Notice: Subject to any disclaimer, the term of this patent is extended or adjusted under 35 U.S.C. 154(b) by 1297 days.

(21) Appl. No.: 10/770,350

(22) Filed: Feb. 2, 2004

(65) Prior Publication Data
US 2005/0038340 A1    Feb. 17, 2005

Related U.S. Application Data

(60) Continuation-in-part of application No. 10/166,795, filed on Jun. 7, 2002, now Pat. No. 6,716,184, which is a division of application No. 09/397,471, filed on Sep. 17, 1999, now Pat. No. 6,425,867.

(60) Provisional application No. 60/100,812, filed on Sep. 18, 1998.

(51) Int. Cl.
*A61B 8/00* (2006.01)
*A61N 7/00* (2006.01)
(52) U.S. Cl. .............................. 600/439; 601/2; 600/458
(58) Field of Classification Search ................. 600/439, 600/473, 476, 458; 604/20; 601/2, 3
See application file for complete search history.

(56) References Cited

U.S. PATENT DOCUMENTS 5,039,774 A    8/1991    Shikinami et al. ............. 528/60

(Continued)

FOREIGN PATENT DOCUMENTS

DE            04230415 A1    3/1994

(Continued)

OTHER PUBLICATIONS

Ebbini, Emad S. Image-guided noninvasive surgery with ultrasound phased arrays. SPIE vol. 3249 (1998) p. 230-239.*

(Continued)

*Primary Examiner*—Eric F Winakur
*Assistant Examiner*—Helene Bor
(74) *Attorney, Agent, or Firm*—Ronald M. Anderson

(57) ABSTRACT

Ultrasound contrast agents are used to enhance imaging and facilitate HIFU therapy in four different ways. A contrast agent is used: (1) before therapy to locate specific vascular structures for treatment; (2) to determine the focal point of a HIFU therapy transducer while the HIFU therapy transducer is operated at a relatively low power level, so that non-target tissue is not damaged as the HIFU is transducer is properly focused at the target location; (3) to provide a positive feedback mechanism by causing cavitation that generates heat, reducing the level of HIFU energy administered for therapy compared to that required when a contrast agent is not used; and, (4) to shield non-target tissue from damage, by blocking the HIFU energy. Various combinations of these techniques can also be employed in a single therapeutic implementation.

30 Claims, 24 Drawing Sheets

U.S. PATENT DOCUMENTS

| | | | | |
|---|---|---|---|---|
| 5,065,742 | A | 11/1991 | Belikan et al. | 128/24 |
| 5,215,680 | A * | 6/1993 | D'Arrigo | 516/11 |
| 5,394,877 | A | 3/1995 | Orr et al. | 600/459 |
| 5,474,071 | A | 12/1995 | Chapelon et al. | 600/439 |
| 5,507,790 | A | 4/1996 | Weiss | 607/100 |
| 5,522,878 | A | 6/1996 | Montecalvo et al. | 607/152 |
| 5,536,489 | A * | 7/1996 | Lohrmann et al. | 424/9.52 |
| 5,558,092 | A * | 9/1996 | Unger et al. | 600/439 |
| 5,762,066 | A * | 6/1998 | Law et al. | 600/439 |
| 5,827,204 | A | 10/1998 | Grandia et al. | 601/2 |
| 5,833,647 | A | 11/1998 | Edwards | 604/22 |
| 5,846,517 | A * | 12/1998 | Unger | 424/9.52 |
| 5,853,752 | A * | 12/1998 | Unger et al. | 424/450 |
| 5,906,580 | A * | 5/1999 | Kline-Schoder et al. | 600/459 |
| 5,993,389 | A * | 11/1999 | Driscoll et al. | 600/371 |
| 6,039,694 | A | 3/2000 | Larson et al. | 600/459 |
| 6,071,239 | A | 6/2000 | Cribbs et al. | 600/439 |
| 6,179,831 | B1 | 1/2001 | Bliweis | 606/21 |
| 6,267,734 | B1 | 7/2001 | Ishibashi et al. | 601/2 |
| 6,409,720 | B1 | 6/2002 | Hissong et al. | 606/27 |
| 6,425,867 | B1 | 7/2002 | Vaezy | 600/439 |
| 6,491,672 | B2 | 12/2002 | Slepian et al. | 604/267 |
| 6,548,047 | B1 * | 4/2003 | Unger | 424/9.51 |
| 6,551,576 | B1 * | 4/2003 | Unger et al. | 424/9.52 |
| 6,595,934 | B1 | 7/2003 | Hissong et al. | 601/3 |
| 6,599,256 | B1 | 7/2003 | Acker et al. | 601/2 |
| 6,626,855 | B1 | 9/2003 | Weng et al. | 601/3 |
| 6,656,136 | B1 | 12/2003 | Weng et al. | 601/2 |
| 6,676,601 | B1 | 1/2004 | Lacoste et al. | 600/439 |
| 6,685,639 | B1 | 2/2004 | Wang et al. | 600/439 |
| 6,716,184 | B2 | 4/2004 | Vaezy et al. | |
| 6,719,699 | B2 | 4/2004 | Smith | 600/459 |
| 6,846,291 | B2 | 1/2005 | Smith et al. | 600/459 |
| 6,875,420 | B1 * | 4/2005 | Quay | 424/9.52 |
| 2002/0016557 | A1 * | 2/2002 | Duarte et al. | 601/2 |
| 2002/0193681 | A1 | 12/2002 | Vitek et al. | 600/411 |
| 2002/0193831 | A1 | 12/2002 | Smith, III | 607/2 |
| 2003/0018255 | A1 | 1/2003 | Martin et al. | 600/437 |
| 2003/0069569 | A1 | 4/2003 | Burdette et al. | 606/27 |
| 2003/0125623 | A1 | 7/2003 | Kelly et al. | 600/437 |
| 2004/0019278 | A1 | 1/2004 | Abend | 600/545 |
| 2004/0030268 | A1 | 2/2004 | Weng et al. | 601/2 |
| 2004/0078034 | A1 | 4/2004 | Acker et al. | 606/27 |
| 2004/0097805 | A1 | 5/2004 | Verard et al. | 600/428 |
| 2004/0097840 | A1 | 5/2004 | Holmer | 601/2 |
| 2004/0143186 | A1 | 7/2004 | Anisimov et al. | 600/437 |
| 2004/0153126 | A1 | 8/2004 | Okai | 607/1 |
| 2004/0181178 | A1 | 9/2004 | Aldrich et al. | 601/3 |
| 2004/0234453 | A1 | 11/2004 | Smith | 424/9.5 |
| 2004/0254620 | A1 | 12/2004 | Lacoste et al. | 607/96 |

FOREIGN PATENT DOCUMENTS

| | | |
|---|---|---|
| EP | 01265223 B1 | 11/2002 |
| WO | WO 00/72919 | 12/2000 |

OTHER PUBLICATIONS

Indman, Paul, MD,. "Alternatives in Gynecology." Hysteroscopy© 2000 OBGYN.net <http://www.gynalternatives.com/hsc.html>.

Kaczkowski, Peter J., Vaezy, Shahram, Martin, Roy, Crum, Lawrence,. "Development of a High Intensity Focused Ultrasound System for image-guided ultrasonic surgery." Ultrasound for Surgery 2001. <http://cimu.apl.washington.edu/hifusurgerysystem.html>.

Physicians. "Breast Cancer—Insightec: focused ultrasound for non invasive treatment." FAQ <http://www.exablate2000.com/physicians_faq.html>.

Yu, T., Wang, G., Hu, K., Ma, P., Bai, J., and Wang, Z. "A microbubble agent improves the therapeutic efficiency of high intensity focused ultrasound: a rabbit kidney study." (Abstract) NDN 234-0481-1539-3. *Urol Res*. Feb. 2004;32(1): 14-9. Epub Dec. 4, 2003.

Ostensen, Jonny, PhD. "Characterization and Use of Ultrasound Contrast Agents" Acad Radiol 2002; 9(suppl 2); S276-S278.

"Mechanical Bioeffects in the prescence of gas/carrier ultrasound contrast agents." J Ultrasound Med. 19: 120/142, 2000.

Anand, Ajay et al. "Using the ATL 1000 to Collect Domodulated RF Data for Monitoring HIFU Lesion Formation." Center for Industrial and Medical Ultrsound, University of Washington. Abstract. 11pp., 2003.

Brayman, Andrew A., Lizotte, Lynn M., Miller, Morton W. "Erosion of Artificial Endothelia In Vitro by Pulsed Ultrasound: Acoustic Pressure, Frequency, Membrane Orientation and Microbubble Contrast Agent Dependence." Ultrasound in Med. & Biol., vol. 25, No. 8, pp. 1305/1320, 1999. Copyright 1999 World Federation for Ultrasound in Medicine & Biology.

Chen, Wen/Shiang, et al. "A comparison of the fragmentation thresholds and inertial cavitation doses of different ultrasound contrast agents." J. Acoust. Soc. Am. 113 (1), Jan. 2003: pp. 643/651.

Chen, Wen/Shiang, et al. "Inertial Cavitation Dose and Hemolysis Produced in Vitro with or Without Optison." Ultrasound in me. & Biol., vol. 29, No. 5, pp. 725/737, 2003.

Dayton, Paul, A., et al. "The magnitude of radiation force on ultrasound contrast agents." J. Acoust. Soc. Am. 112 (5) Pt. 1, Nov. 2002: pp. 2183/2192.

Everbach, Carr, E. and Charles W. Francis. "Cavitational Mechanisms in Ultrasound/Accelerated Thrombolysis at 1 MHz." Ultrasound in Med. & Biol., vol. 26, No. 7, pp. 1153/1160, 2000. Copyright 2000 World Federation in Medicine and Biology.

Guzman, Hector R., et al. "Ultrasound—Mediated Disruption of Cell Membranes. I. Quantification of Molecular uptake and Cell Viability." J. Acoust. Soc. Am. 110 (1), Jul. 2001: pp. 588/595.

Guzman, Hector R., et al. "Ultrasound/mediated disruption of cell membranes. II. Heterogeneous effects on cells." J. Acoust. Soc. Am 110 (1), Jul. 2001: pp. 597/606.

Hatangadi, Ram Bansidhar. "A Novel Dual Axis Multiplanar Transesophageal Ultrasound Probe for Three-Dimensional Echocardiograph." *University of Washington, Department of Sciences and Engineering*. (1994), Abstract. vol. 55-11B: 4960pp.

Holt, Glynn, R., Roy, Ronald, A., Edson, Patrick A., Yang, Xinmai. "Bubbles and Hifu: the Good, the Bad and the Ugly." *Boston University, Department of Aerospace and Mechanical Engineering*, Boston, MA 02215: 120/131.

Hynynen, Kullervo, et al. "Potential Adverse Effects of High/Intensity Focused Ultrasound Exposure on Blood Vessels in Vivo." Ultrasound in Med. & Biol., vol. 22, No. 2, pp. 193/201, 1996.

Ka/yun Ng, Yang Liu. "Therapeutic Ultrasound: Its Application in Drug Delivery." Medicinal Research Reviews, vol. 22, 204/223, 2002 © 2002 John Wiley & Sons, Inc.

Miller, Morton W. et al. "A Review of In Vitro Bioeffects of Intertial Ultrasonic Cavitation From a mechanistic Perspective." Ultrasound in Med & Biol., vol. 22, No. 9, pp. 1131/1154, 1996.

Nobuki Kudo, Takehiro Miyaoka, Kengo Okada, and Katsuyuki Yamamoto. "Study on Mechanism of Cell Damage Caused by Microbubbles Exposed to Ultrasound." *Graduate School of Engineering, Hokkaido University, Japan, Research Institute for Electronic Science, Hokkaido University*, 060/0812 Japan.

Owaki, T., Nakano, S. Arimura, K., Aikou, T. "The Ultrasonic Coagulating and Cutting System Injuries Nerve Function." *First Department of Surgery, Kagoshima University School of Medicine, Kagoshima, Japan, Endoscopy*. (2002) 575/579.

Poliachik, Sandra L., et al. "Activation, Aggregation and Adhesion of Platelets Exposed to High/Intensity Focused Ultrasound." Ultrasound in Med. & Biol., vol. 27, No. 11, pp. 1567/1576, 2001.

Poliachik, Sandra L., et al. "Effect of High -Intensity Focused Ultrasound on Whole Blood with or without Microbubble Contrast Agent." Ultrasound in Med. & Biol., vol. 25, No. 6, 1999: 991/998.

Porter, T.R., Xie, F. "Ultrasound, Microbubbles and Thrombolysis." Progress in Cardiovascular Diseases, vol. 44, No. 2, Oct. 2001: 101/110.

Rivens, I.H., Rowland, I.J., Denbow, M., Fisk, N. M., Harr, G.R., Leach, M.O. "Vascular occlusion using focused ultrasound surgery for use in fetal medicine." *European Journal of Ultrasound 9* (1999): 89/97.

Rosenschein, Uri, et al. "Ultrasound Imaging/Guided Nonivasive Ultrasound Thrombolysis/Preclinical Results." © 2000 American Heart Association, Inc. (Circulation. 2000;102:238/245.) <http://www.circulationaha.com.org>.

Rosenschein, Uri, et al. "Shock/Wave Thrombus Ablation, A New Method for Noninvasive Mechanical Thrombolysis." The American Journal of Cardiology, vol.70, Issue 15, Nov. 1992: pp. 1358/1361.

Tachibana, Katsuro and Shunro MD., PhD. "The Use of Ultrasound for Drug Delivery." *First Department of Anatomy, Fukuoka University School of Medicine*, Nanakuma, Japan, Echocardiography. (2001) 323/328.

Tachibana, Katsuro, and Shunro M.D., Ph.D. "Albumin Microbubble Echo/Contrast Material as an Enhancer for Ultrasound Accelerated Thrombolysis." (Circulation, 1995;92: 1148/1150.) © 1995 American Heart Association, Inc.

Vaezy, Shahram et al. 2001. "Acoustic surgery." *Physics World* (August): 35/39.

Vaezy, Shahram et al. 2001. "Experimental Investigations and Device Development." First International Workshop on the Application of HIFU in Medicine. (May 10/13): 4pp.

\* cited by examiner

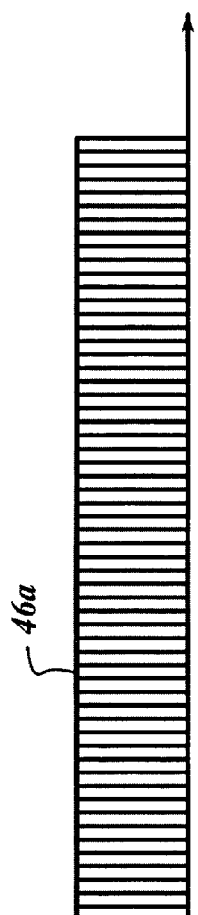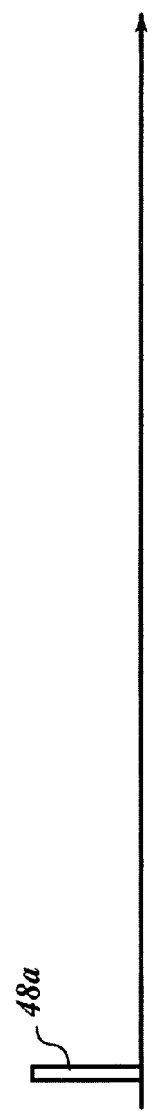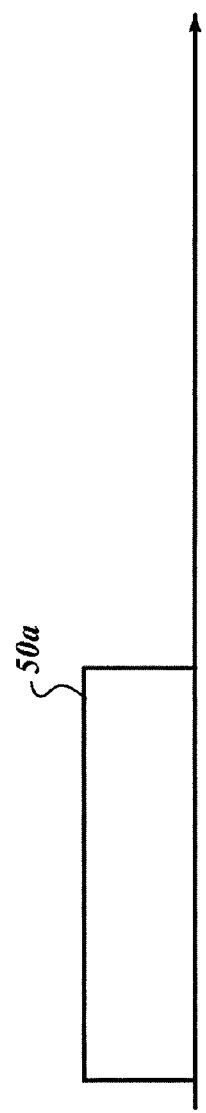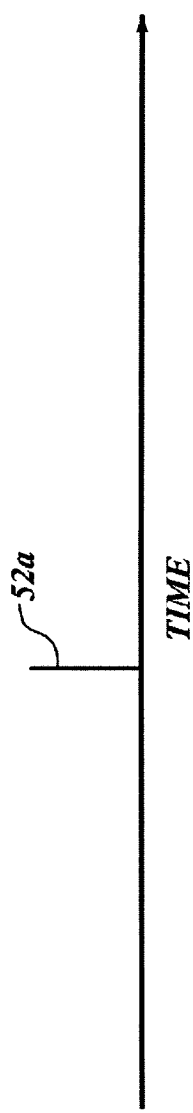
Fig 3A(1)
Fig 3A(2)
Fig 3A(3)
Fig. 3A(4)

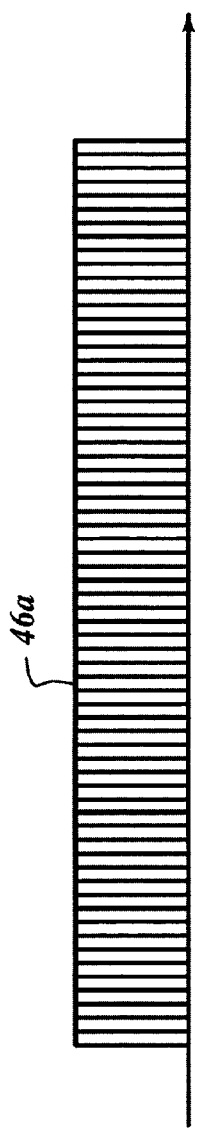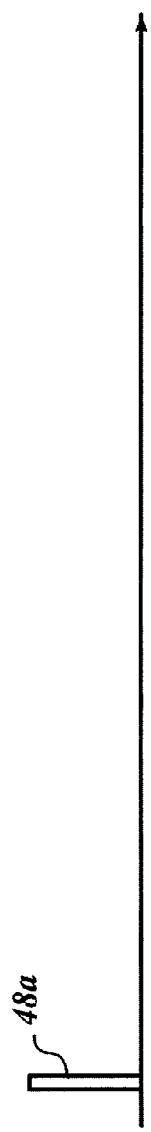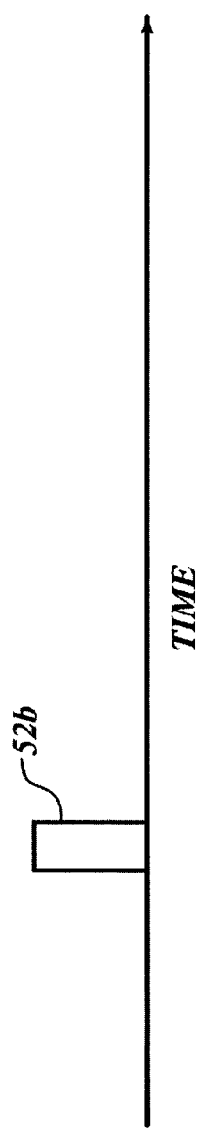
Fig. 3B(1) Fig. 3B(2) Fig. 3B(3) Fig. 3B(4)

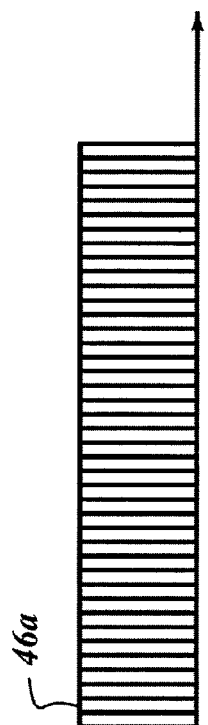
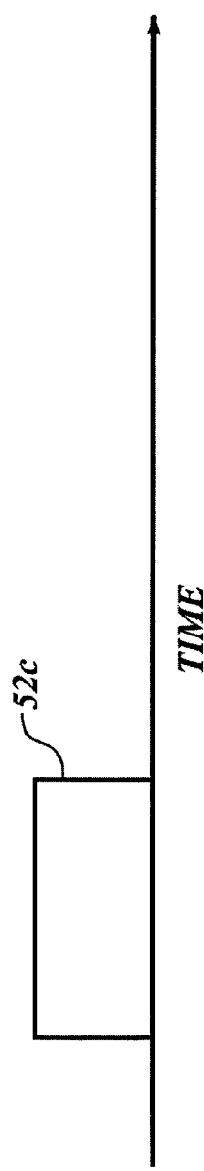
Fig 3C(1)
Fig 3C(2)
Fig 3C(3)
Fig. 3C(4)

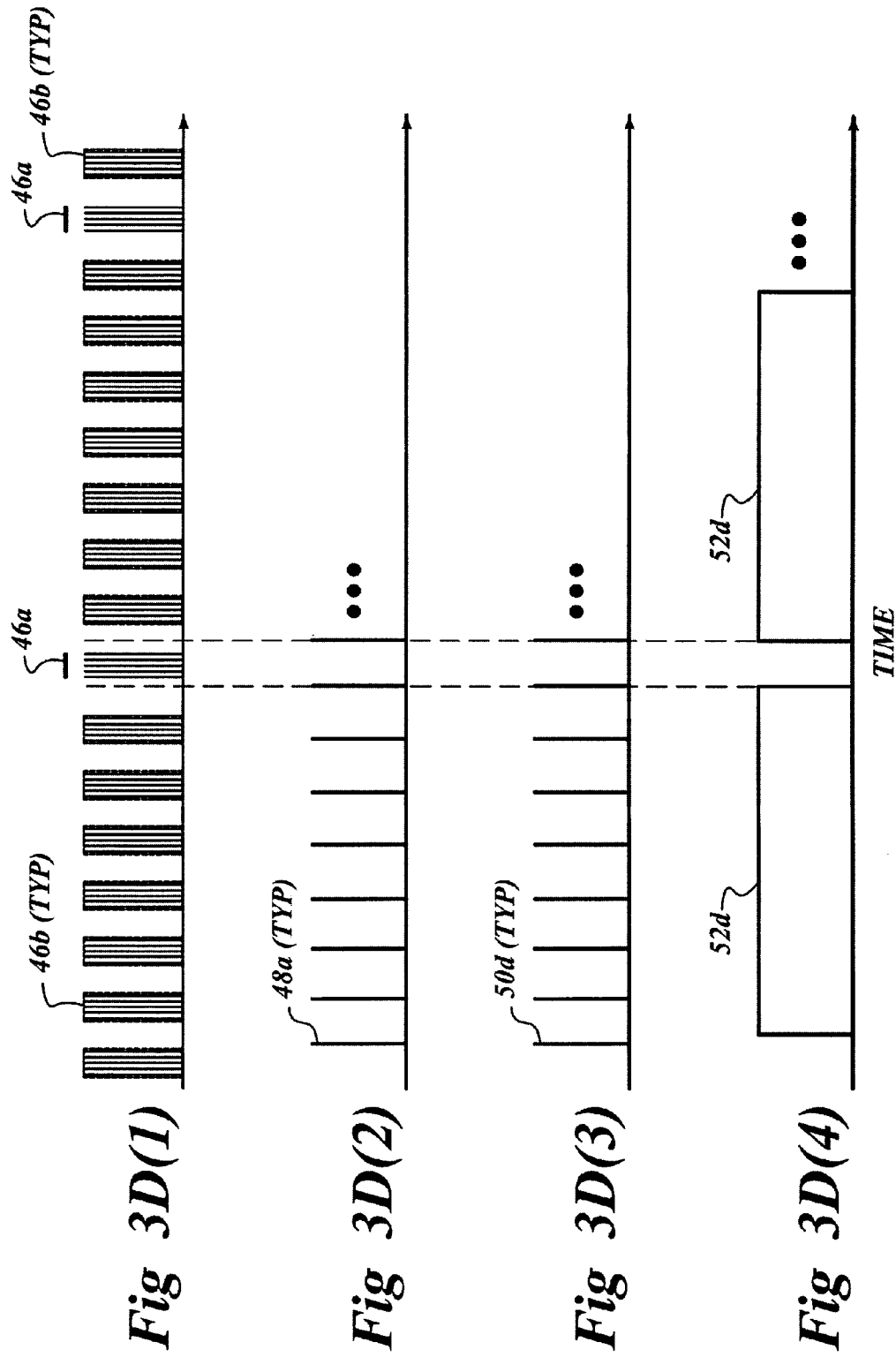

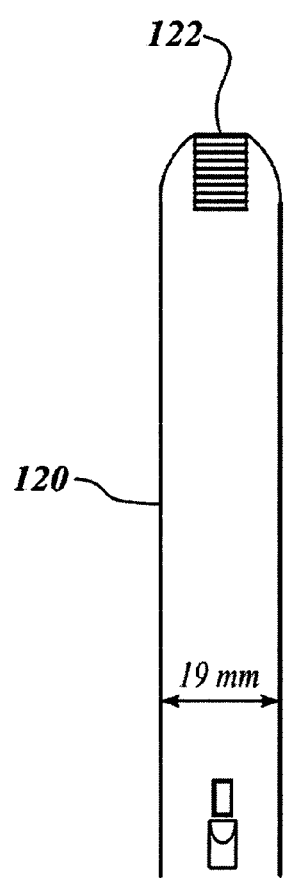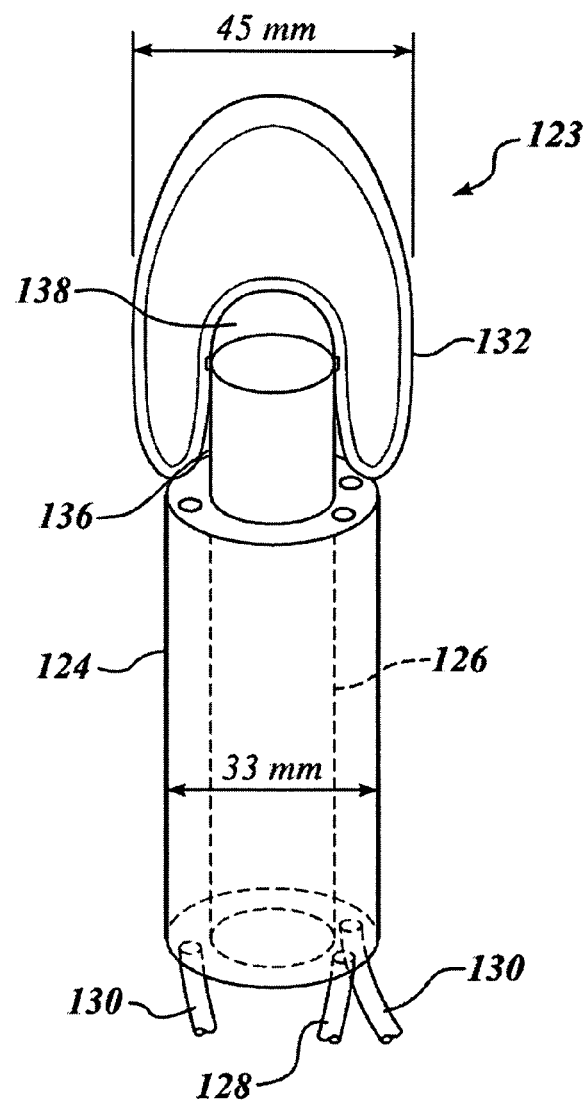
Fig. 9A
*(PRIOR ART)*
Fig. 9B

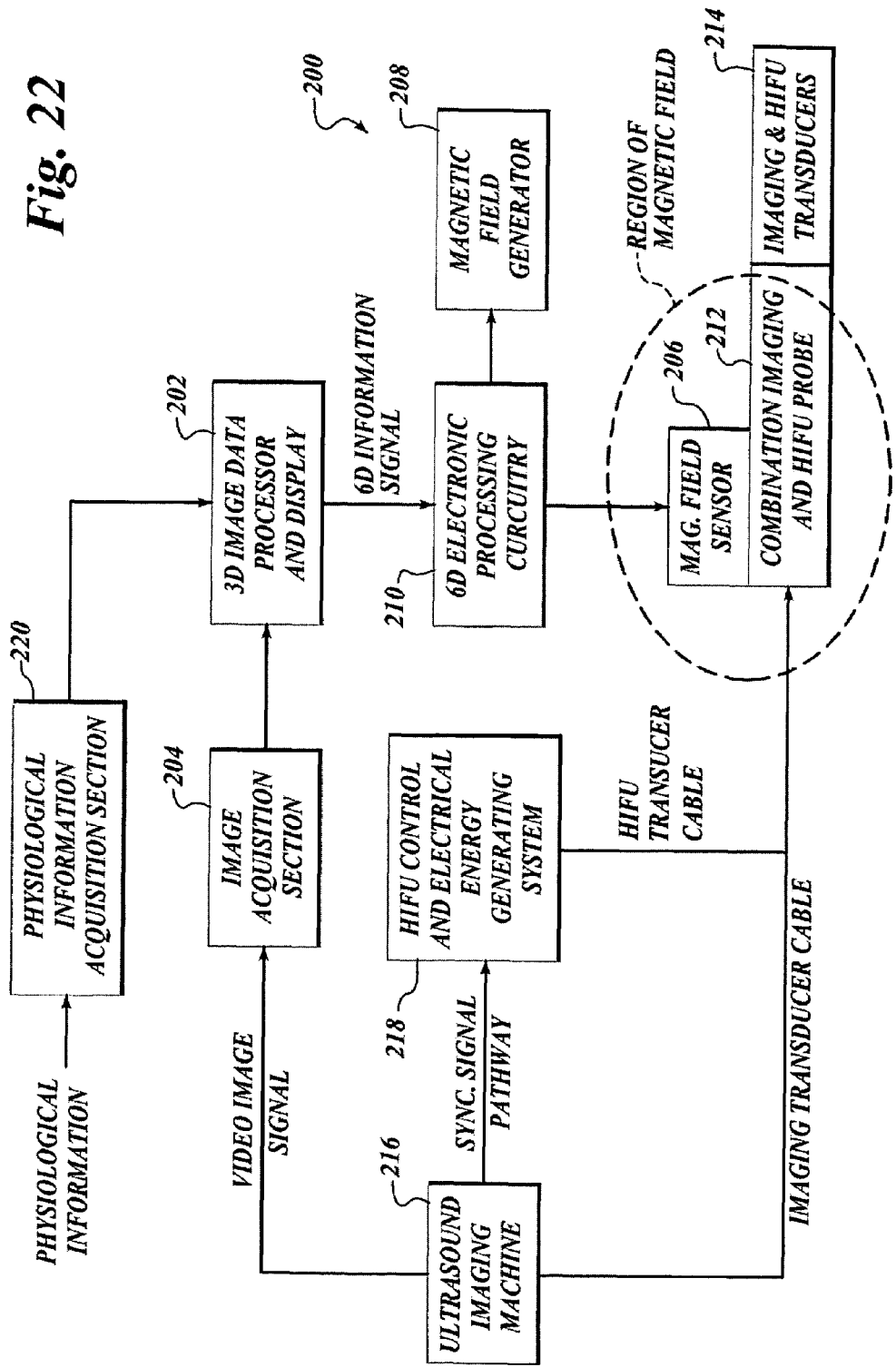

USE OF CONTRAST AGENTS TO INCREASE THE EFFECTIVENESS OF HIGH INTENSITY FOCUSED ULTRASOUND THERAPY

RELATED APPLICATIONS

This application is a continuation-in-part application of prior application Ser. No. 10/166,795, filed on Jun. 7, 2002 now U.S. Pat. No. 6,716,184, which itself is a divisional application of prior application Ser. No. 09/397,471, filed on Sep. 17, 1999 and now issued as U.S. Pat. No. 6,425,867, which is based on a prior provisional application Ser. No. 60/100,812, filed on Sep. 18, 1998, the benefits of the filing dates of which are hereby claimed under 35 U.S.C. § 119(e) and 35 U.S.C. § 120.

GOVERNMENT RIGHTS

This invention was made with U.S. Government support under Contract N00014-96-0630 awarded by the United States Department of Defense. The U.S. Government has certain rights in the invention.

FIELD OF THE INVENTION

The present invention generally relates to the use of ultrasound contrast agents to enhance therapy utilizing high intensity focused ultrasound, and more specifically, relates to the use of contrast agents to enhance localization of a vascular system and to facilitate and enhance a therapeutic treatment provided using high intensity ultrasound.

BACKGROUND OF THE INVENTION

Ultrasound has gained acceptance as an imaging technique particularly well suited to providing information about a patient's internal structures without risk of exposure to potentially harmful radiation, as may occur when using X-ray imaging techniques. The first recorded use of ultrasound as an imaging technique was by Dr. Karl Dussik, a Psychiatrist at the hospital in Bad Ischl, Austria; who tried to locate brain tumors using ultrasound. He used two opposed probes, including one that transmitted ultrasound waves, while the other probe received them. With these probes, he transmitted an ultrasound beam through a patient's skull, and used the received signal to visualize the cerebral structure by measuring the ultrasound beam attenuation. He published his technique in 1942, in an article entitled, "Hyperphonography of the Brain."

Specially manufactured medical diagnostic equipment using ultrasound became available in the 1950's. An ultrasound examination is a safe diagnostic procedure that uses very high-frequency sound waves to produce an image of the internal structures of the body. Many studies have shown that these sound waves are harmless and may be used with complete safety, even on pregnant women, where the use of X-rays would be inappropriate. Furthermore, ultrasound examinations are sometimes quicker and typically less expensive than other imaging techniques.

More recently, the use of high intensity focused ultrasound (HIFU) for therapeutic purposes, as opposed to imaging, has received significant attention in the medical community. HIFU therapy employs ultrasound transducers that are capable of delivering 1,000-10,000 W/cm$^2$ at a focal spot, in contrast to diagnostic ultrasound where intensity levels are usually below 0.1 W/cm$^2$. A portion of the mechanical energy from these high intensity sound waves is transferred to the targeted location as thermal energy. The amount of thermal energy thus transferred can be sufficiently intense to cauterize tissue, or to cause tissue necrosis (by inducing a temperature rise to beyond 70° C.) without actual physical charring of the tissue. Tissue necrosis can also be achieved by mechanical action alone (i.e., by cavitation that results in mechanical disruption of the tissue structure). Further, where the vascular system supplying blood to an internal structure is targeted, HIFU can be used to induce hemostasis. The focal point of this energy transfer can be tightly controlled so as to obtain tissue necrosis in a small target area without damaging adjoining tissue. Thus, deep-seated tumors can be destroyed with HIFU without surgical exposure of the tumor site.

A particular advantage of HIFU therapy over certain traditional therapies is that HIFU is less invasive. The current direction of medical therapy is progressively toward utilizing less-invasive and non-operative approaches, as will be evident from the increasing use of laparoscopic and endoscopic techniques. Advantages include reduced blood loss, reduced risk of infection, shorter hospital stays, and lower health care costs. HIFU has the potential to provide an additional treatment methodology consistent with this trend by offering a method of non-invasive surgery. HIFU enables transcutaneous tumor treatment without making a single incision, thus avoiding blood loss and the risk of infection. Also, HIFU therapy may be performed without the need for anesthesia, thereby reducing surgical complications and cost. Most importantly, these treatments may be performed on an outpatient basis, further reducing health care cost, while increasing patient comfort.

The use of HIFU for the destruction of tumors is a relatively new technique. The first clinical trials were performed on patients with hyperkinetic and hypertonic disorders (symptoms of Parkinson's disease). HIFU was used to produce coagulation necrosis lesions in specific complexes of the brain. While the treatment was quite successful, monitoring and guidance of the HIFU lesion formation was not easily achieved (N. T. Sanghvi and R. H. Hawes, "High-intensity focused ultrasound," *Gastrointestinal Endoscopy Clinics of North America*, vol. 4, pp. 383-95, 1994). The problem has been that the high energy therapeutic wave introduces a significant amount of noise into an ultrasound imaging signal employed to monitor the treatment site, making simultaneous imaging and treatment difficult. Indeed, the high energy of the HIFU can completely overwhelm conventional ultrasonic imaging systems. However, the advancement of imaging modalities has provided grounds for renewed research and development of HIFU-based tumor treatment methods. In general, current methods involve the use of discrete imaging and therapeutic steps, i.e., a treatment site is first imaged, therapy is applied, and the treatment site is again imaged. The therapeutic transducer is de-energized during the imaging process to eliminate the noise it would otherwise produce. However, the time required for carrying out each of these discrete steps has prevented the significant potential of HIFU from being fully realized, since real-time guidance and monitoring of HIFU has not been achieved.

Two HIFU-based systems have been developed for the treatment of benign prostatic hyperplasia (BPH) in humans (E. D. Mulligan, T. H. Lynch, D. Mulvin, D. Greene, J. M. Smith, and J. M. Fitzpatrick, "High-intensity focused ultrasound in the treatment of benign prostatic hyperplasia," *Br J Urol*, vol. 70, pp. 177-80, 1997). These systems are currently in clinical use in Europe and Japan, and are undergoing clinical trials in the United States. Both systems use a transrectal HIFU probe to deliver 1,000-2,000 W/cm$^2$ to the prostate tissue through the rectum wall. No evidence of damage to the rectal wall has been observed during a rectoscopy, performed immediately after HIFU treatment (S. Madersbacher, C. Kratzik, M. Susani, and M. Marberger, "Tissue ablation in benign prostatic hyperplasia with high intensity focused ultrasound," *Journal of Urology*, vol. 152, pp. 1956-60; discussion 1960-1, 1994). Follow-up studies have shown decreased symptoms of BPH (i.e., increased urinary flow rate, decreased post-void residual volume, and decreased symptoms of irritation and obstruction; see S. Madersbacher, C. Kratzik, N. Szabo, M. Susani, L. Vingers, and M. Marberger, "Tissue ablation in benign prostatic hyperplasia with high-intensity focused ultrasound," *European Urology*, vol. 23 Supplement 1, pp. 39-43, 1993). In this prior art use of HIFU, ultrasound imaging is employed to obtain pre- and post-treatment maps of the prostate and the treatment area. Significantly, the noise induced in the imaging signal by the HIFU prevents real time imaging of the treatment site. Therefore, strict imaging requirements, such as no patient movement during the entire procedure (thus, the need for general or spinal anesthesia), limit the performance of these systems. It should be noted that respiration alone can result in sufficient patient movement so that the HIFU is no longer targeted as precisely as would be desired. Especially where the treatment site is adjacent to critical internal structures that can be damaged, the lack of real time imaging is a significant drawback to an otherwise potentially very useful treatment methodology.

HIFU has also been studied for the de-bulking of malignant tumors (C. R. Hill and G. R. ter Haar, "Review article: high intensity focused ultrasound—potential for cancer treatment," *Br J Radiol*, vol. 68, pp. 1296-1303, 1995). Prostate cancer (S. Madersbacher, M. Pedevilla, L. Vingers, M. Susani, and M. Marberger, "Effect of high-intensity focused ultrasound on human prostate cancer in vivo," *Cancer Research*, vol. 55, pp. 3346-51, 1995) and testicular cancer (S. Madersbacher, C. Kratzik, M. Susani, M. Pedevilla, and M. Marberger, "Transcutaneous high-intensity focused ultrasound and irradiation: an organ-preserving treatment of cancer in a solitary testis," *European Urology*, vol. 33, pp. 195-201, 1998) are among the cancers currently being investigated clinically for potential treatment with HIFU. An extensive clinical study to extracorporeally treat a variety of stage 4 cancers is underway in England (A. G. Visioli, I. H. Rivens, G. R. ter Haar, A. Horwich, R. A. Huddart, E. Moskovic, A. Padhani, and J. Glees, "Preliminary results of a phase I dose escalation clinical trial using focused ultrasound in the treatment of localized tumors," *Eur J Ultrasound*, vol. 9, pp. 11-8, 1999). The cancers involved include prostate, liver, kidney, hipbone, ovarian, breast adenoma, and ocular adenoma. No adverse effects, except one case of skin burn have been observed. Significantly, none of these studies has addressed the noise issue preventing the real time imaging of HIFU treatment.

U.S. Pat. No. 5,471,988 teaches the combination of a HIFU therapy transducer and an imaging transducer on the same probe. This patent points out that one of the problems with the prior art has been obtaining scanning data in conjunction with the therapeutic operation of the probe, due to the noise that the therapeutic wave introduces into the imaging signal. The reference notes that a problem with non-simultaneous imaging is that in the time frame between when the image was last seen, and when the therapy transducer is energized, it is possible that the probe will move relative to a target area. Thus, the therapeutic energy may be applied to an area that is not the desired target. The patent teaches that it is desirable for the therapy and imaging transducers operate at different frequencies, e.g., 12 MHz for the imaging transducer and less than 2 MHz for the therapeutic transducer. It is also suggested that incorporating noise reduction circuitry in the imaging system can help to reduce the impact of the interfering noise. Unfortunately, it has been determined that this approach does not work as effectively as would be desired.

U.S. Pat. No. 5,769,790 describes another combination probe that includes transducers for both ultrasonic imaging and treatment. This patent teaches that prior to the delivery of therapy, verification of the focal point of the therapeutic wave is needed and advocates energizing the therapy transducer at a relatively low power level and using the imaging transducer to detect the low power ultrasound waves produced by the therapy transducer that are reflected from the target site. This technique provides a B-mode image where the only area in the image to be significantly illuminated is the focus of the therapy transducer. The image frame can then be interleaved with or super imposed on a normal B-mode image frame where both transmit and receive functions are performed using the imaging transducer. Once the focal point of the therapy transducer has been verified in this manner, therapy can be delivered by applying higher power, longer duration excitation to the therapy transducer. Significantly, the '790 patent does not teach the simultaneous scanning of the treatment area with the ultrasonic signal transmitted by the imaging transducer while the therapy transducer is operational, nor does the '790 patent discuss how the noise problem can be addressed.

U.S. Pat. No. 5,895,356 is directed to a method and apparatus optimized for the treatment of diseases of the prostate. This reference teaches that the echogenicity of tissue heated to over 60° C. changes so that when imaged using an ultrasonic imaging transducer, a bright spot appears in the viewing field, and that this echogenicity is transient (it fades with time). The patent also teaches storing the location of this region of higher echogenicity in a memory of an imaging system and superimposing the known focal point of the therapeutic transducer on the display of the imaging system, so that the therapeutic transducer can be focused on an area of interest prior to energizing the therapeutic transducer. The patent teaches imaging using low power ultrasound, focusing using the known focal point, ceasing the imaging, applying a higher power ultrasound therapy, ceasing the therapy, and then using low power ultrasound to generate an image of the area just treated. Significantly, the patent does not discuss how noise produced by the simultaneous operation of imaging and therapeutic ultrasound can be reduced.

While the prior art has recognizes the advantages that real time imaging can provide, a suitable method of achieving such imaging has not been described. It would be desirable to provide a method in which simultaneous imaging and therapy can be achieved in real time without a noise signal degrading the image quality of the treatment site.

Furthermore, there are many medical conditions that could benefit from simultaneous treatment and imaging using HIFU. In particular, it appears that the treatment of gynecological and obstetrical disorders could be significantly enhanced. For example, uterine fibroids, which are benign tumors of the uterus found in more than half of all women, could be treated using an image-guided HIFU therapy system. Approximately 30% of all hysterectomies are related to these uterine fibroids. Current treatment methods for uterine fibroids include both drug therapy and surgery. Drug therapy has virtually a 100% rate of tumor reoccurrence once the drug therapy has stopped, and the drug therapy itself includes numerous negative side effects. The rate of reoccurrence is significantly less (about 15%) for the surgical therapy, though the surgical procedure is invasive, requiring a significant recovery period, and involves significant risks, such as blood loss, damage to related organs, and the ever present risk of infection. It is estimated that uterine fibroid procedures in the United States alone account for 1.2 to 3.6 billion dollars in annual medical costs.

Contrast agents have been successfully employed to enhance diagnostic imaging in magnetic resonance imaging (MRI), and it has been suggested that gaseous micro-bubbles might be useful contrast agents for use in conjunction with diagnostic ultrasound. It would therefore be desirable to provide a method for employing contrast agents for use in connection with the administration of therapeutic HIFU. Further, it would be desirable to develop a simultaneous or real-time imaging and therapeutic ultrasound method and corresponding apparatus that beneficially employ contrast agents.

SUMMARY OF THE INVENTION

The present invention uses ultrasound contrast agents to enhance ultrasound imaging and the use of therapeutic ultrasound. Preferably, ultrasound is concurrently employed to image a target area and to provide therapy to a treatment site within the target area. In general, ultrasound contrast agents are either solutions including a plurality of small bubbles, or liquids that can be induced to generate such bubbles in-vivo. In particular, volatile liquids can be beneficially employed to generate such bubbles in-vivo, since the thermal or ultrasound energy required to induce a volatile liquid to generate bubbles is normally lower than the thermal or ultrasound energy that would damage tissue.

A first aspect of the invention employs contrast agents to map a vascular system associated with a target area before HIFU therapy is initiated, to facilitate selection of a specific portion of the target area to be treated using HIFU. Imaging ultrasound is used to observe the progress of the contrast agent as it propagates through a vascular system associated with the target area. Because blood flow in a tumor is generally distinguishable from blood flow in normal tissue, tumors can readily be identified in this fashion. Major vessels blood vessels can be distinguished from minor blood vessels, so that the major blood vessels of a tumor can be targeted and destroyed using HIFU, thereby depriving the tumor of nutrients and oxygen. Such a map can also indicate damaged or leaking blood vessels that can be treated with HIFU (i.e., cauterized) to stop the leakage. Once a target is identified, HIFU therapy can be used to treat the selected target.

A second aspect of the invention is directed at the use of contrast agents to enable the focal point of a HIFU beam to be identified, without a risk of damaging non-target tissue. If an improperly focused HIFU beam is energized at a therapeutic power level, inadvertent damage can occur to tissue improperly targeted by the HIFU beam. Non-target tissue can be destroyed, and non-target blood vessels can be cauterized, interrupting blood flow to normal tissue that was improperly targeted. To minimize the risk of such an occurrence, a contrast agent is introduced into the target area before the HIFU beam is energized at full power. The therapeutic ultrasonic transducer system is initially energized at a level that is insufficient to damage tissue, but is sufficiently energetic to induce the contrast agent to produce a change in the echogenicity of tissue at the treatment site. The change in echogenicity enables the focal point of the therapeutic ultrasonic transducer system to be accurately directed at the tissue to be treated. Liquids that can be induced to generate bubbles in-vivo are particularly useful for this function of the invention. A volatile liquid that can be induced to generate bubbles in response to the application of low power levels of HIFU is particularly preferred, since the lower the power level of the HIFU beam when the desired treatment site is being determined, the less chance there is of any inadvertent damage to non-target tissue. The position of the therapeutic ultrasonic transducer is manipulated until the focal point corresponds to a desired treatment site (such as a portion of the vascular system of the target identified using the first aspect of the invention), and the energy level of the therapeutic wave is increased to a therapeutic level that is sufficiently energetic to produce a desired therapeutic effect.

A third aspect of the invention is directed to the use of contrast agents to reduce the HIFU energy level required to achieve a therapeutic effect. Liquids exposed to ultrasound energy at certain ultrasound frequencies respond by cavitating. Cavitation generates heat, which raises the temperature of the surrounding tissue and the liquid. The increased temperature reduces the energy required to induce further cavitation, which produces even more heating. Thus, this process provides a positive feedback effect that results in the highly efficient conversion of acoustic energy to heat and reduces the amount of HIFU energy required to heat tissue to a temperature sufficient to cause tissue damage and necrosis.

Yet another aspect of the invention involves using the reflective characteristics of ultrasound contrast agents as a shield to prevent a HIFU beam from reaching underlying non-target tissue. This aspect of the invention occurs because contrast agents reflect acoustic energy. Thus, the careful imposition of contrast agents proximate a treatment site will shield underlying non-target tissue from damage. If insufficient liquid volume naturally occurs in an area in which it is desired to introduce a contrast agent to act as a shield, the required liquid volume and contrast agent can be infused. In general, care must be taken to ensure that the contrast agent is not disposed between the treatment site and the therapeutic ultrasonic transducer, or the HIFU will be shielded from the treatment site, when operated at a desired power. Under some circumstances, it may be desirable to dispose some contrast agent between the treatment site and the therapeutic ultrasonic transducer to reduce the amount of acoustic energy delivered to the treatment site; however, contrast agents will more often be advantageously employed to shield tissue disposed beyond or to the sides of the treatment site (relative therapeutic ultrasonic transducer), to protect tissue disposed in such areas from the HIFU beam.

Any two or more of the various aspects of the invention described above can be advantageously combined to enhance a therapy session.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIGS. 1A-1C respectively illustrate ultrasonic images generated during the simultaneous use of ultrasound for imaging and therapy according to the prior art, the pulsing of the HIFU in a conventional scanned image, and the synchronized pulsing of the HIFU and the scan image so as to shift the noise away from a displayed treatment site;

FIG. 2 is a block diagram illustrating the components of a system capable of simultaneously using ultrasound for imaging and therapy, in accord with the present invention;

FIGS. 3A(1)-3D(4) illustrate timing and synchronization patterns that enable the simultaneous use of ultrasound for imaging and therapy;

FIG. 4 illustrates yet another timing and synchronization pattern for synchronizing the HIFU and imaging scans;

FIGS. 5A and 5B respectively illustrate a schematic view of individual external imaging and therapeutic ultrasonic transducers being used for the simultaneous imaging and treatment of a tumor in a female reproductive system, and an ultrasonic image that would thus be generated;

Figure 10:
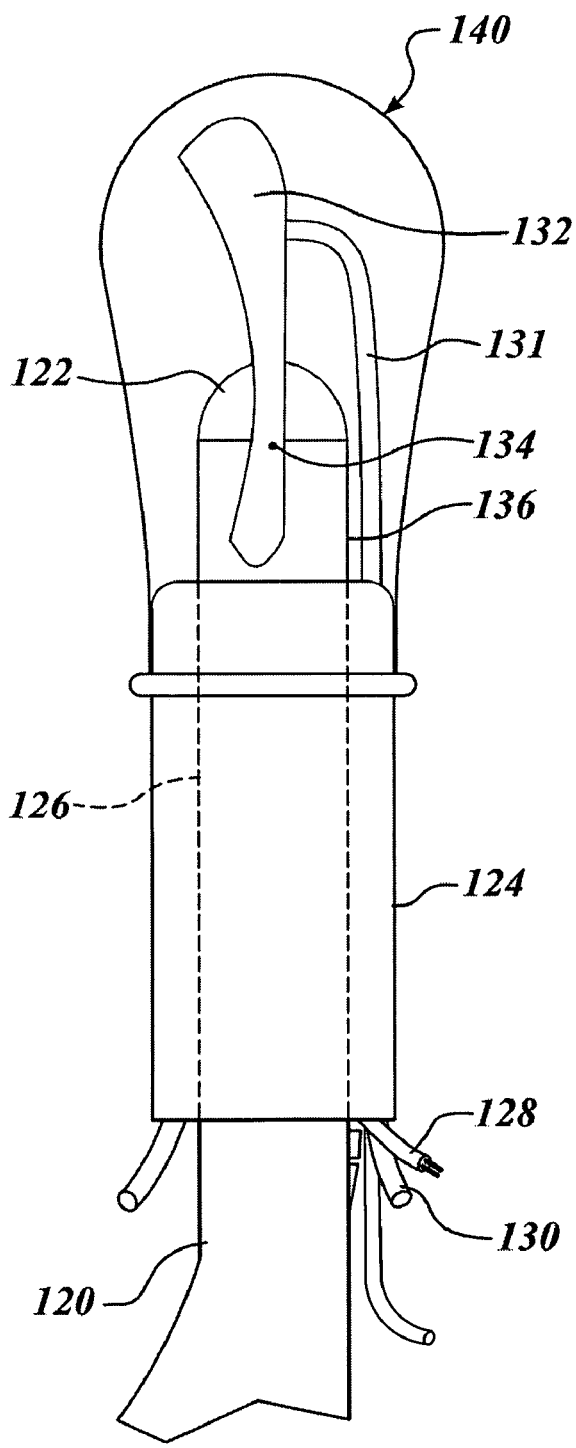
Figure 11:
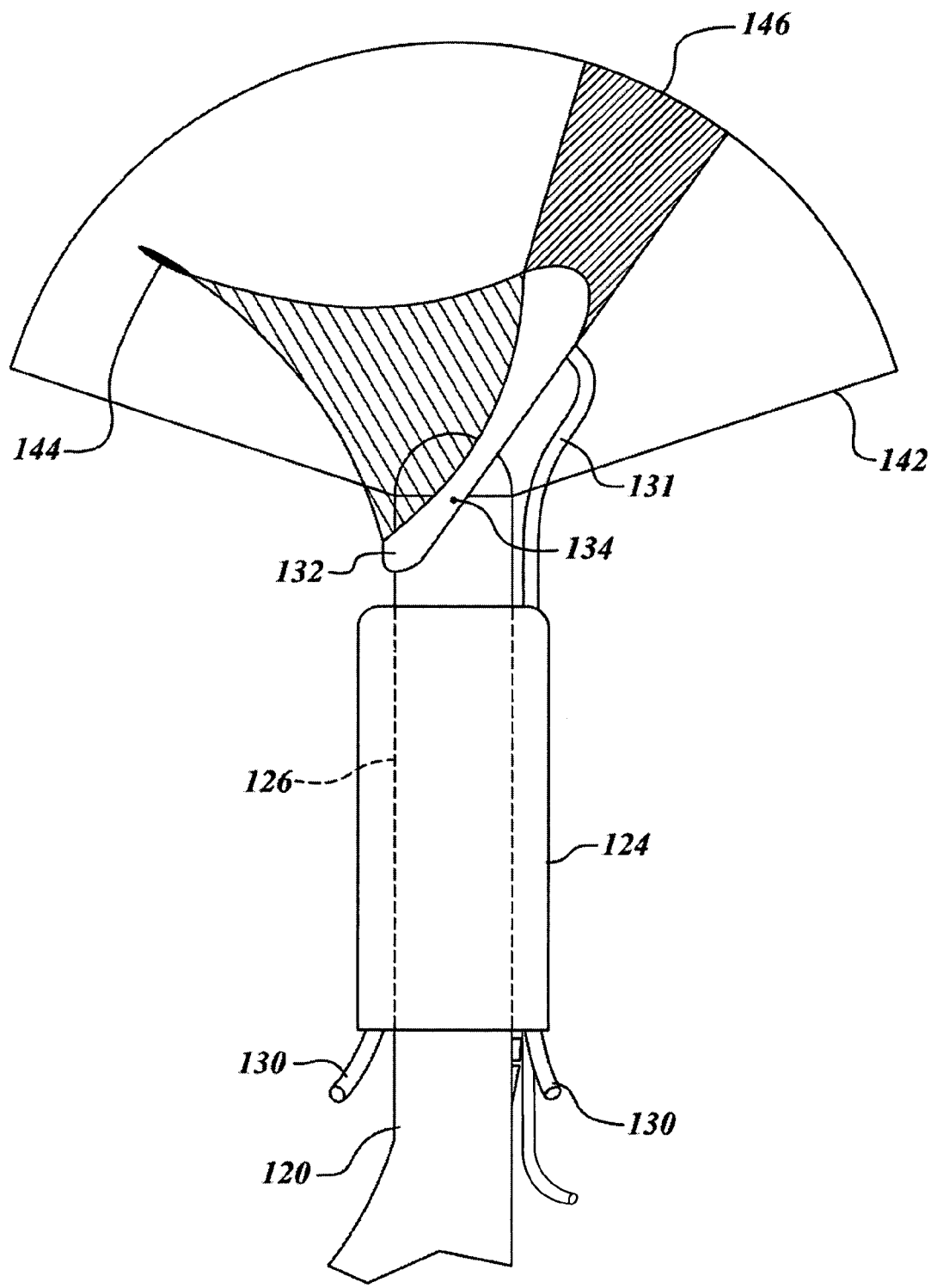
Figure 12:
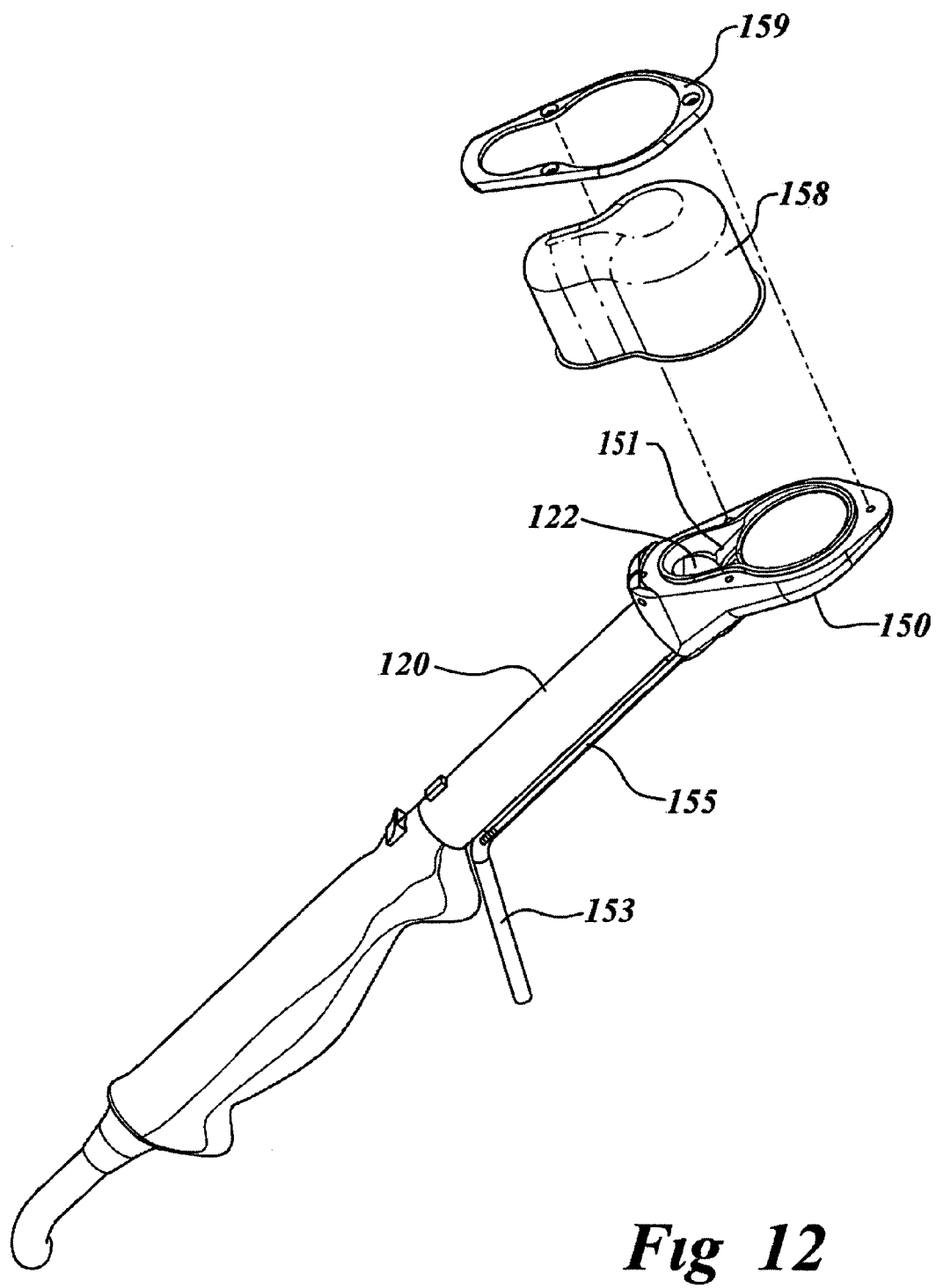
Figure 13:
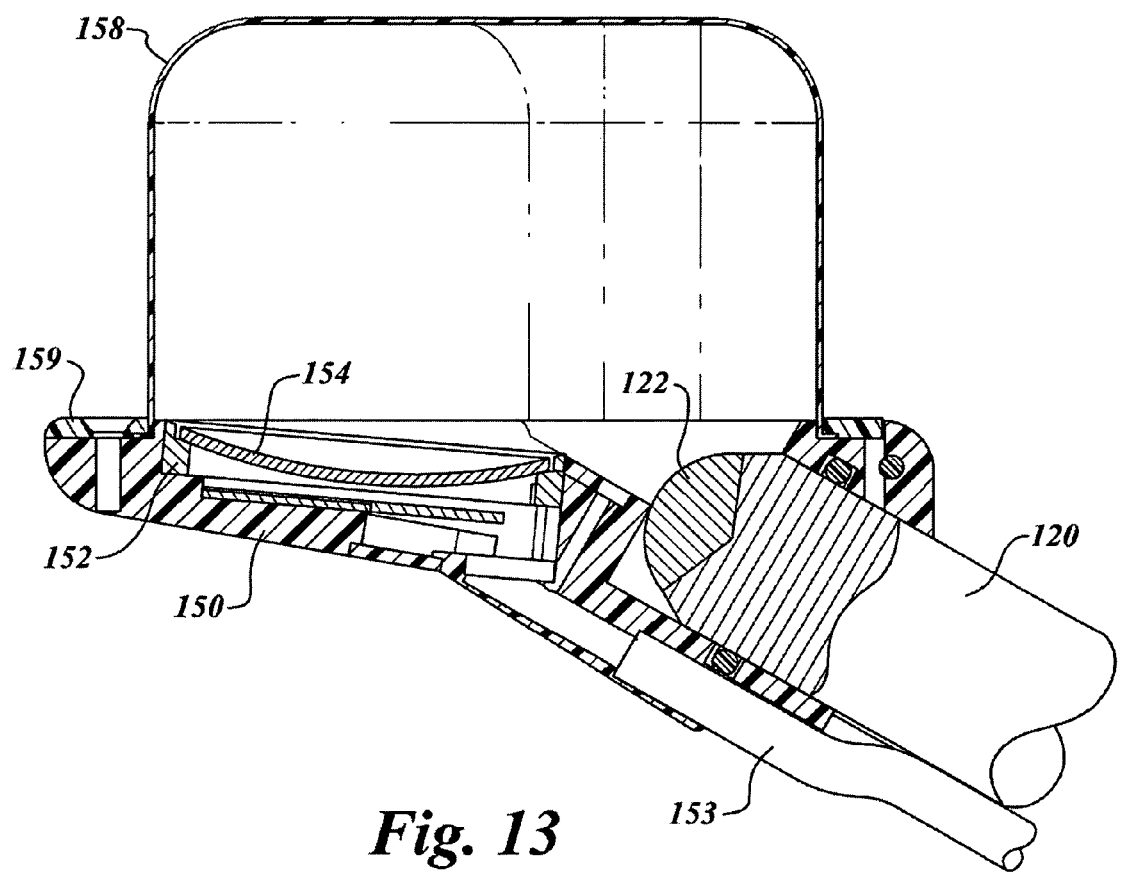
Figure 14:
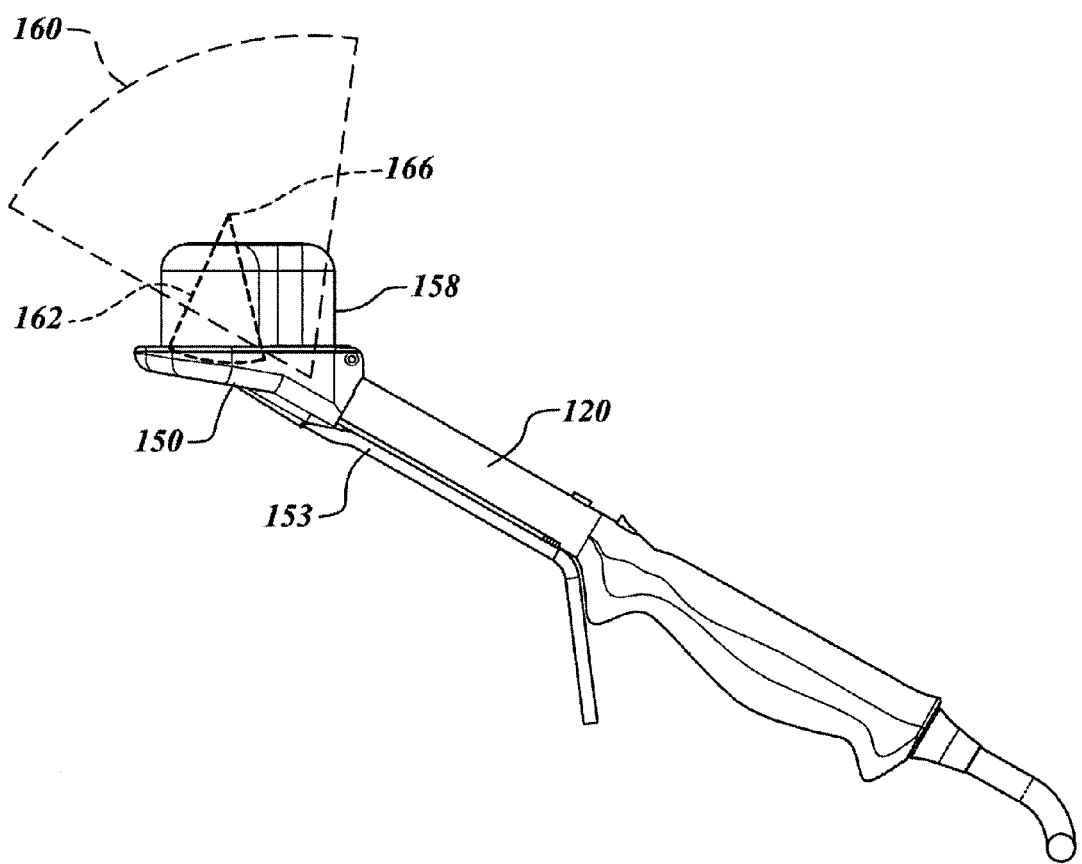
Figure 15:
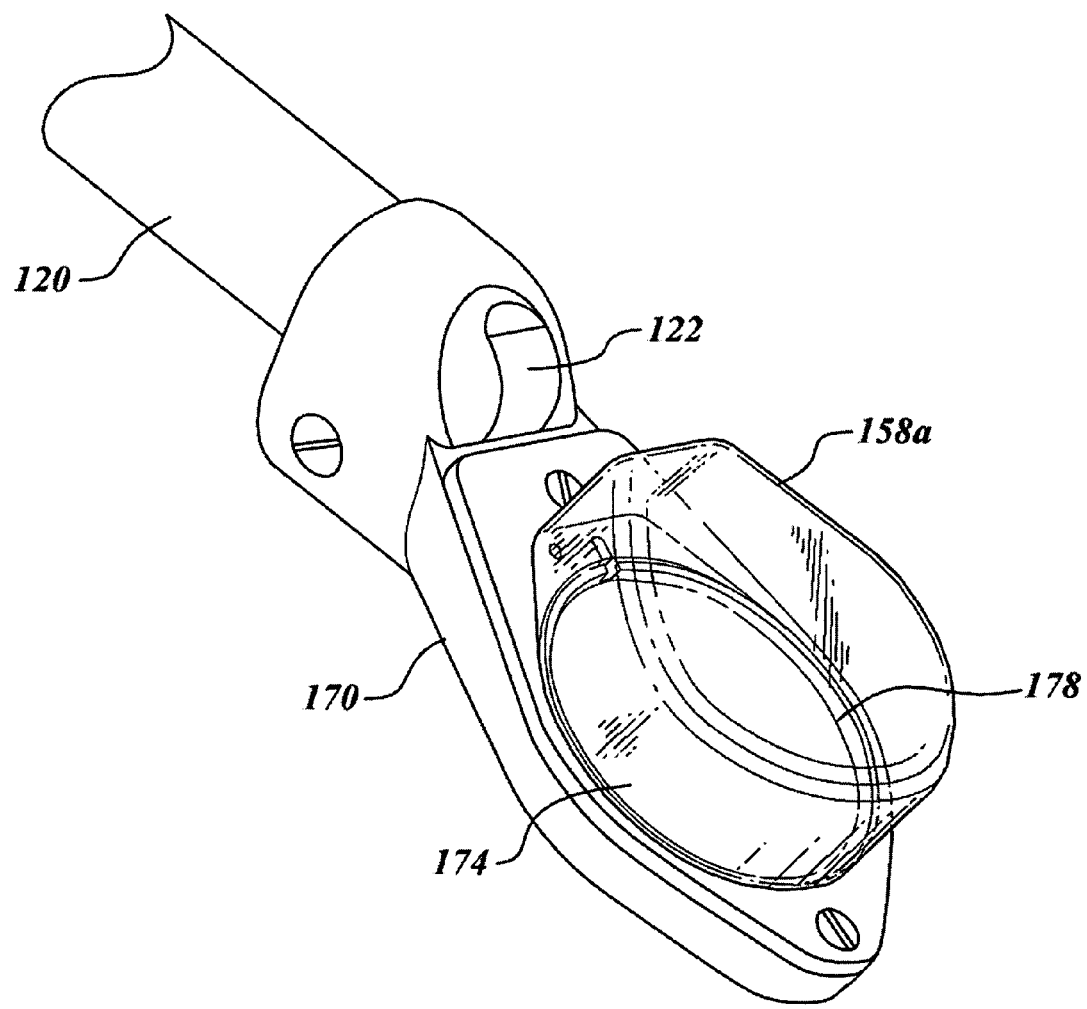
Figure 16:
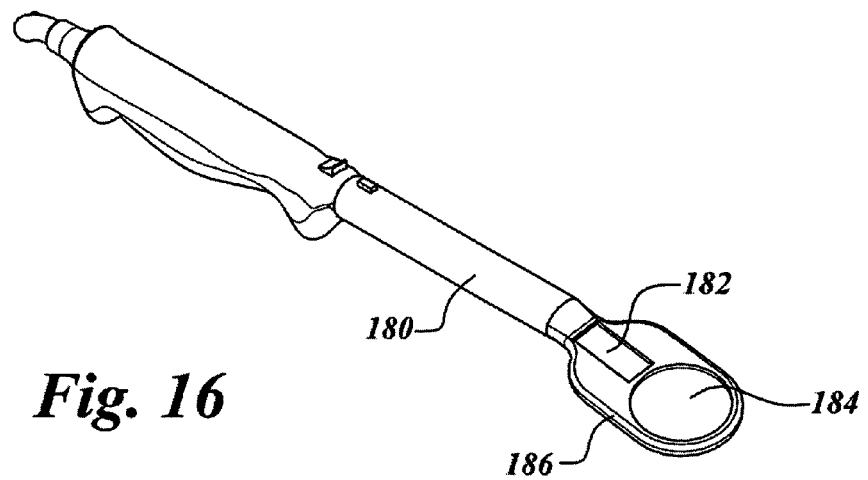
Figure 17:
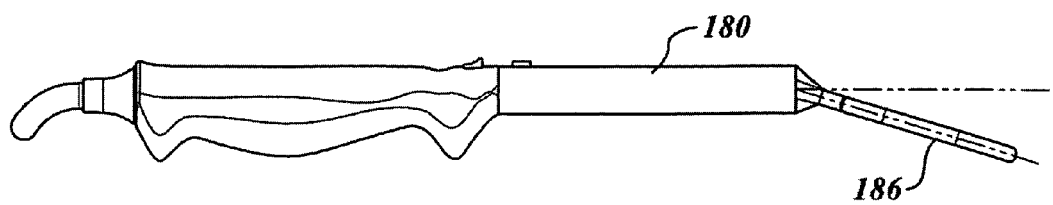
Figure 18:
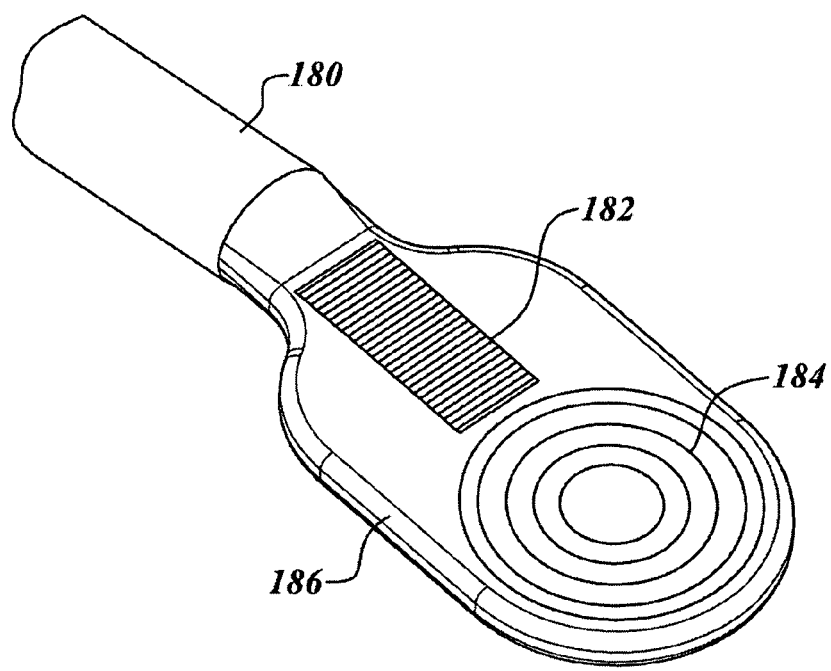
Figure 19:
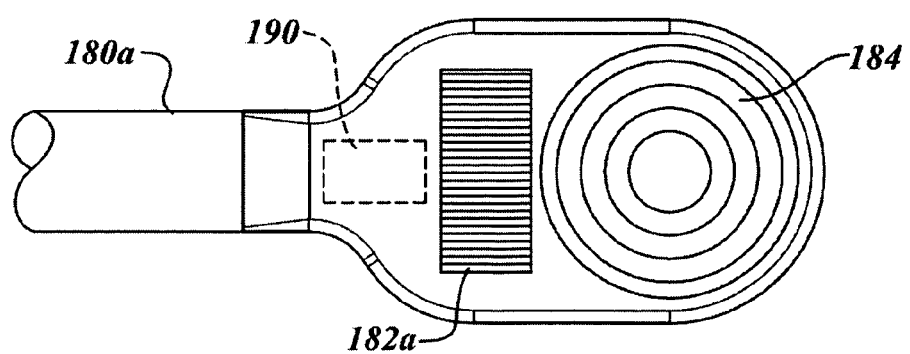
Figure 20:
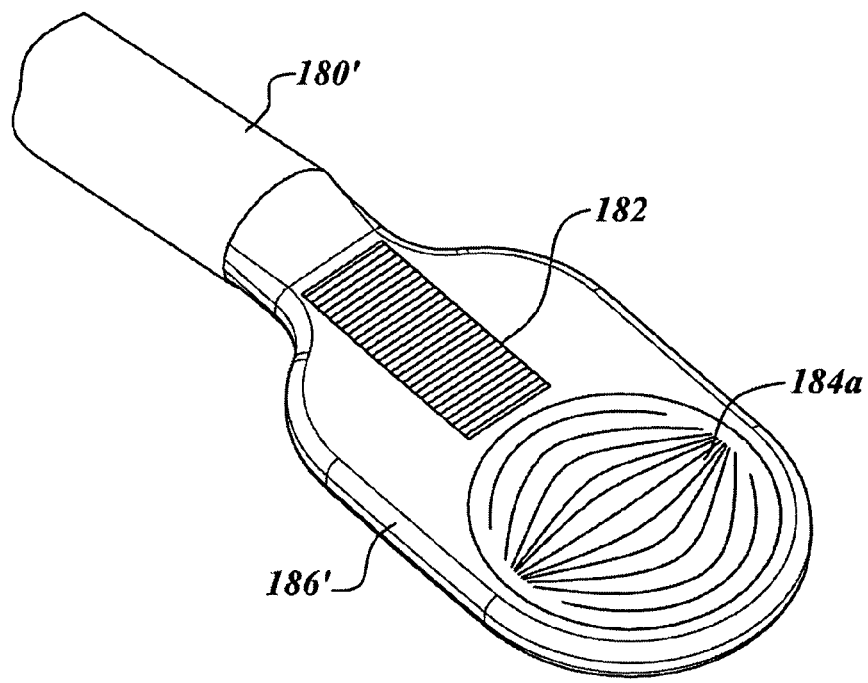
Figure 21:
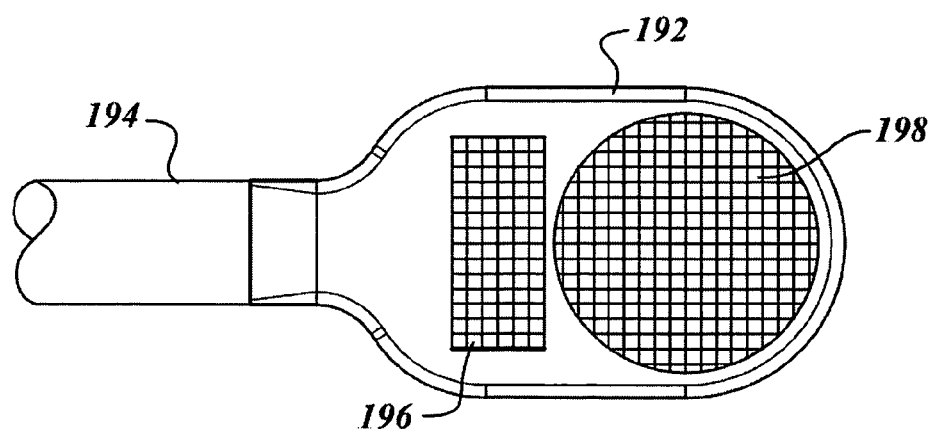
Figure 23A:
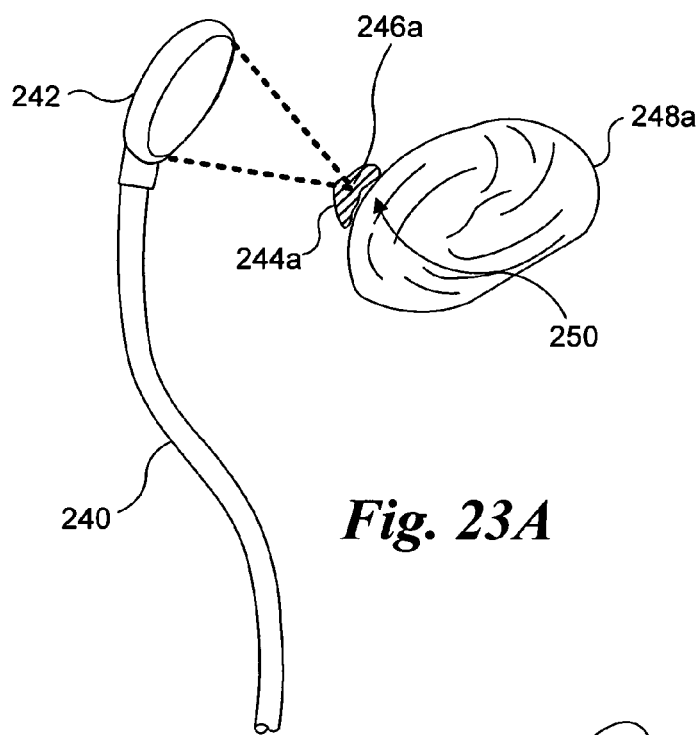
Figure 23B:
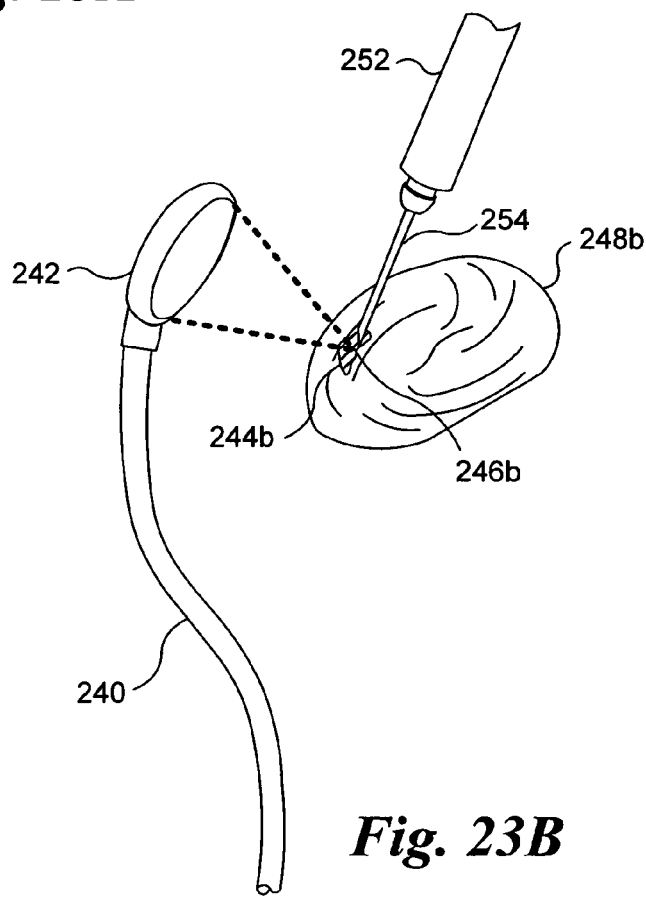
Figure 24A:
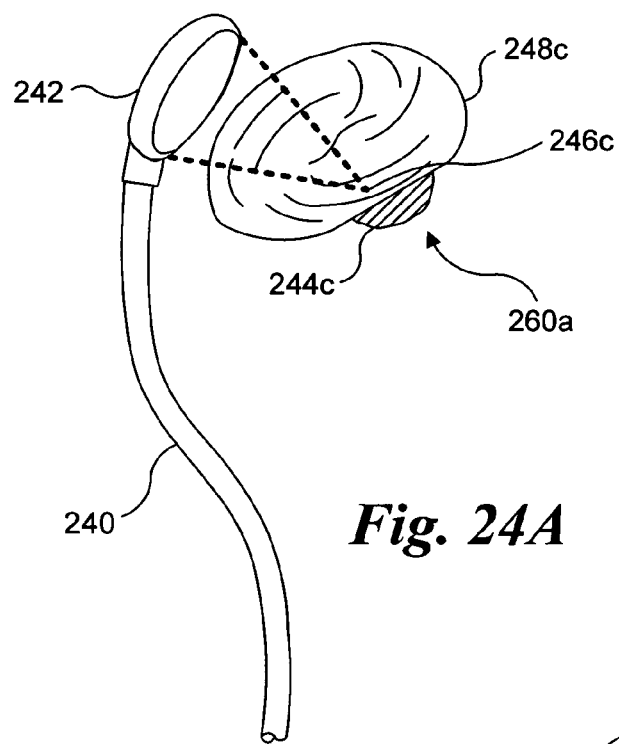
Figure 24B:
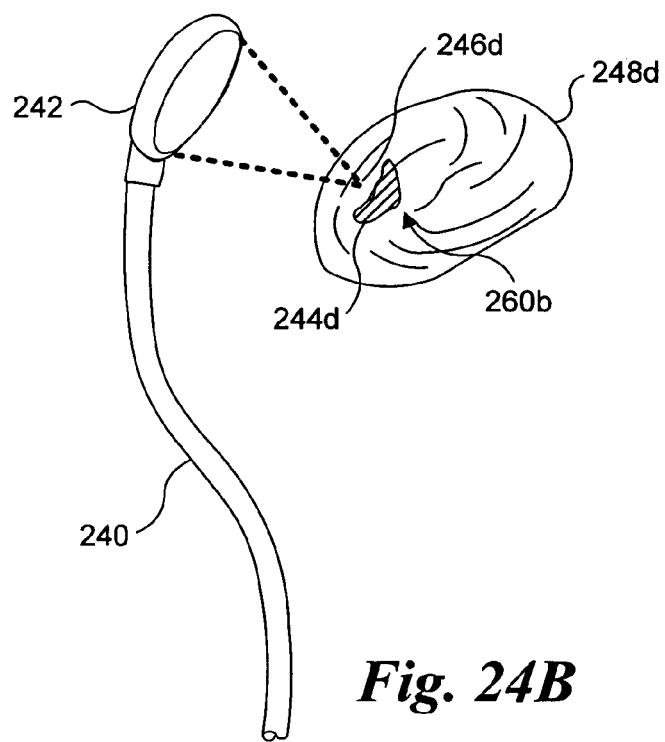

FIGS. 9A and 9B respectively illustrate a schematic view of the distal end of a vaginal probe, and a HIFU module adapted to be used in conjunction with the vaginal probe;

FIG. 10 is a schematic view of a HIFU module mounted onto the distal end of a prior art vaginal probe;

FIG. 11 is a schematic view of a combination HIFU module and prior art vaginal probe, and an ultrasonic image produced thereby in which the focal point of the HIFU module is displayed in a noise-free area of the image, in accord with the present invention;

FIG. 12 is a schematic view of a second embodiment of a HIFU module combined with a prior art vaginal probe;

FIG. 13 is a cross-sectional view of the second embodiment of the combination HIFU module and prior art vaginal probe shown in FIG. 12, including a chamber in fluid communication with both the imaging and therapeutic transducers;

FIG. 14 is a schematic view of the second embodiment of the combination HIFU module and prior art vaginal probe shown in FIGS. 12 and 13, including the fluid filled chamber and the wave patterns of both the imaging and therapeutic transducers;

FIG. 15 is a schematic view of a third embodiment of a HIFU module combined with a prior art vaginal probe, including a chamber in fluid communication with only the therapeutic transducer;

FIG. 16 is a schematic view of therapeutic and imaging transducers integrated into a vaginal probe that includes a paddle-shaped distal end;

FIG. 17 is a side elevational view of the integrated probe of FIG. 16 illustrating how a position of the paddle-shaped head can be varied around a pivot joint;

FIG. 18 is a schematic view of phased array therapeutic and imaging transducers of the integrated probe of FIG. 16, in which the imaging transducer is steerable, and the focal point of the therapeutic transducers is variable;

FIG. 19 is a schematic view of a different embodiment of a paddle-headed integrated probe similar to that of FIG. 16, in which the orientation of the imaging transducer has been shifted by 90°, thus shifting the scanning field by 90°;

FIG. 20 is a schematic view of a different embodiment of a paddle-headed integrated probe similar to that of FIG. 18, in which the therapy transducer is steerable in the same plane as the imaging transducer;

FIG. 21 is a schematic view of phased array therapeutic and imaging transducers of an integrated probe in which both the imaging transducer and the therapy transducer are steerable along both their longitudinal and latitudinal axes;

FIG. 22 is a schematic block diagram of a 3D imaging and HIFU therapy system that enables the HIFU therapy to be applied at selected treatment sites in a 3D image of a target area;

FIGS. 23A and 23B schematically illustrate a HIFU therapy probe being used to induce cavitation to enhance HIFU therapy; and FIGS. 24A and 24B schematically illustrate a HIFU therapy probe being used to apply HIFU therapy to a treatment site while an ultrasound contrast agent disposed adjacent to the treatment site serves as a shield, blocking the HIFU beam from propagating beyond the treatment site into non-target tissue.

DESCRIPTION OF THE PREFERRED EMBODIMENT

As noted above in the Background of the Invention, the prior art has recognized that real time imaging of therapeutic HIFU would be beneficial in a number of treatment methodologies. From a practical standpoint this is not proven easy to do, because the HIFU used for therapy completely saturates the signal provided by the imaging transducer. One analogy that might help to make this problem clear relates to the relative intensities of light. Consider the light coming from a star in the evening sky to be equivalent to the low power imaging ultrasound waves that are reflected from a target area toward the imaging transducer, while the light from the sun is equivalent to the HIFU generated by the therapy transducer. When the sun is out, the light from the stars is completely overwhelmed by the light from the sun, and a person looking into the sky is unable to see any stars, because the bright light from the sun completely masks the dim light coming from the stars. Similarly, the HIFU emitted by the therapy transducer completely overwhelms the ultrasonic waves produced by the imaging transducer and any ultrasonic image generated is completely saturated with noise caused by the HIFU from the therapeutic transducer.

Figure 1A:
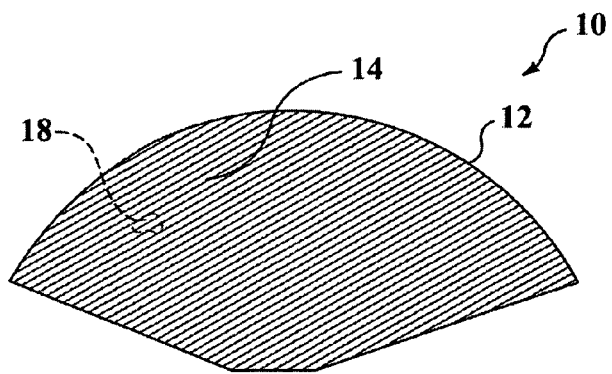

FIG. 1A illustrates an ultrasound image 10 in which a scanned field 12 is completely obscured by noise 14, caused by the simultaneous operation of an imaging pulse and a HIFU wave (neither shown). In ultrasound image 10, a clinician may desire to focus the HIFU wave on a treatment site 18. However, because noise 14 completely saturates scanned field 12, it is impossible to accurately focus the HIFU wave onto treatment site 18. If the therapy transducer is completely de-energized, noise 14 is eliminated from the scanned field. However, under these conditions, the focal point of the HIFU wave will not be seen, and thus, the HIFU wave cannot be accurately focused on treatment site 18. While some change in echogenicity at the HIFU focal point will persist for a time even after the HIFU wave is gone, any change in a position of the therapy transducer (or treatment site 18), would not register until the therapeutic transducer is re-energized, thus the HIFU wave is cannot be focused in real time.

Some prior art systems have included a targeting icon in an ultrasound image to indicate where the known focal point of a specific HIFU transducer would be located in a scanned image. While this icon may be helpful in determining whether the HIFU was previously focused, it still did not enable a clinician to observe real-time results. Once the HIFU therapeutic transducer was energized, the scanned ultrasound image was completely saturated with noise and the clinician could not monitor the progress of the treatment without again de-energizing the HIFU therapeutic transducer.

Figure 1B:
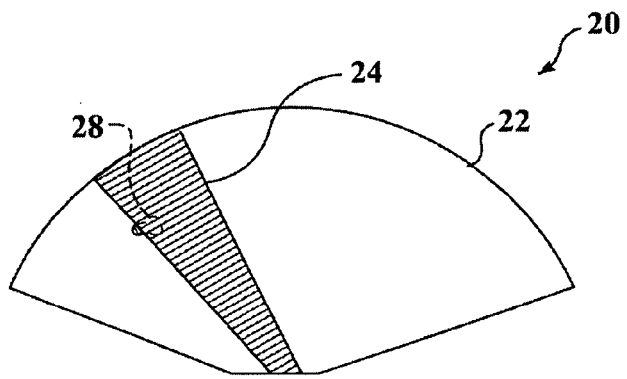

FIG. 1B illustrates one technique in which the amount of noise disrupting the ultrasound image is reduced. In FIG. 1B, the HIFU wave generated by the therapeutic transducer has been pulsed. This technique produces an ultrasound image 20, in which the location of noise 24 in a scanned field 22 is a function of the interference between the pulsed HIFU wave generated by the therapy transducer and the ultrasonic imaging pulses generated by the scanning transducer. In FIG. 1B, noise 24 substantially masks a treatment site 28. This result would not occur in all cases, as to an observer noise 24 would move across scanned filed 22 as the interference between the HIFU waves and the imaging pulses varied in time. Pulsing of the HIFU wave alone would thus allow the clinician to view a noise-free image of the treatment site only when noise 24 was randomly shifted to a different part of scanned field 22, away from the treatment site. However, such pulsing alone generates an image that is extremely distracting to a clinician, as noise 24 flickers across scanned field 22, making it difficult to concentrate and difficult to consistently determine where the focal point of the HIFU wave is relative to the treatment site, in real time.

Figure 1C:
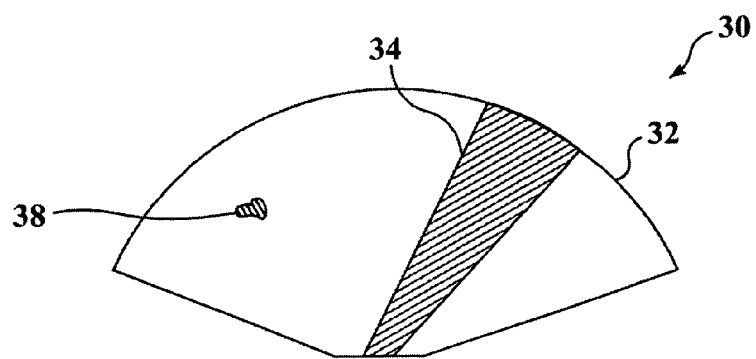

FIG. 1C illustrates an ultrasound image 30 in which a HIFU wave from a therapy transducer has been both pulsed and synchronized with respect to the ultrasonic imaging pulses from an imaging transducer, to ensure that noise 34 does not obscure a treatment site 38. In ultrasound image 30 noise 34 has been shifted to a location within a scanned field 32 that is spaced apart from treatment site 38, by selectively adjusting both the pulsing and the synchronization of the HIFU wave. Preferably, noise 34 is shifted completely away from treatment site 38, thus allowing the clinician a noise-free stable image of treatment site 38 that clearly shows the location of the focal point of the HIFU wave relative to the treatment site. Thus, the HIFU wave can be focused in real time onto treatment site 38, and a clinician can, in real time, view the therapeutic effects of the HIFU wave on treatment site 38. It will be apparent that a clinician can de-energize the therapeutic transducer, thereby ceasing the generation of the HIFU wave as soon as a desired therapeutic effect has been achieved at the treatment site. In this manner, undesired effects on non-target tissue can be minimized.

The terms "therapeutic transducer," "HIFU transducer," and "high intensity transducer," as used herein and in the claims that follow all refer to a transducer that is capable of being energized to produce ultrasonic waves that are much more energetic than the ultrasonic pulses produced by an imaging transducer, and which can be focused or directed onto a discrete location, such as a treatment site in a target area. However, not all ultrasonic waves produced by such a transducer are at a high intensity in at least one embodiment of the present invention, as will be explained below.

Figure 2:
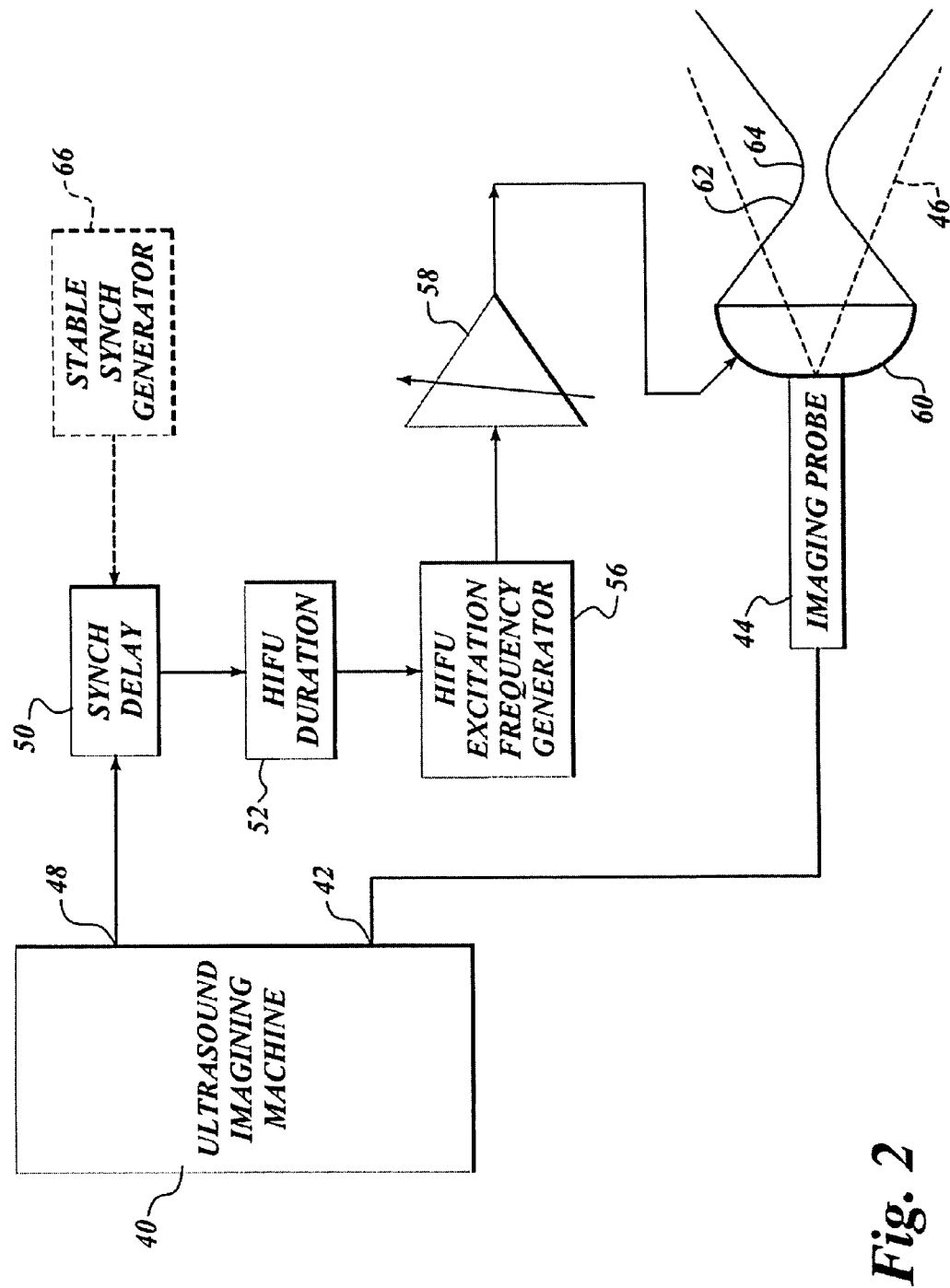

FIG. 2 illustrates a block diagram of an embodiment of the present invention that synchronizes the image and HIFU waves required for the simultaneous imaging and therapy in real time. An ultrasound imaging machine 40 is an ultrasound imaging system of the type that is well known to those of ordinary skill in the art and can be purchased from vendors such as ATL Inc., of Bothell, Wash. An imaging probe 44 that is also of a type well known to those of ordinary skill in the art is connected to ultrasound imaging machine 40 via a cable 42. Imaging probe 44 generates ultrasonic imaging pulses that propagate to the target area, are reflected from structure and tissue within the body, and are received by the imaging probe. The signal produced by the imaging probe in response to the reflected ultrasound waves is communicated to the ultrasound imaging machine through cable 42 and processed to provide a visual representation of the structure and tissue that reflected the ultrasonic imaging pulses. An imaging beam sector 46 from imaging probe 44 is identified in the Figure by dash lines. Also included in the present invention is a therapeutic transducer 60. When excited, this therapeutic transducer generates HIFU waves that are focused at a particular point of interest, i.e., a treatment site within a patient's body. In FIG. 2, the path of a HIFU beam 62 is indicated by dotted lines. HIFU beam 62 narrows to a focal point 64. Those of ordinary skill in the art will recognize that position of focal point 64 relative to therapeutic transducer 60 is a function of the geometry of the therapeutic transducer and will normally depend upon the application. For example, a therapeutic transducer that will be used to apply HIFU therapy to the uterus of a patient from within the vaginal canal (see FIG. 6) will have a different optimum focal point than a therapeutic transducer used to apply treatment to the uterus from outside a patient's body (see FIG. 5).

It should be noted that ultrasound imaging machine 40 differs from prior art systems in several ways, including its inclusion of a synchronization output signal 48. Preferably, ultrasound imaging machine 40 is modified to enable synchronization output signal 48 to be obtained. Because such a synchronization output signal has not been required for prior art ultrasonic imaging applications, provision of a synchronization output signal has generally not been made in prior art ultrasound imaging machines. If a prior art imaging machine that has not been modified to provide synchronization output signal 48 is used, the synchronization output signal can instead be derived from the ultrasonic imaging signal conveyed by cable 42.

Synchronization output signal 48 is supplied to a synchronization delay circuit 50. Synchronization delay circuit 50 enables the user to selectively vary the initiation of each HIFU wave with respect to each sequence of ultrasonic imaging pulses that are generated to form an ultrasonic image. Referring to FIG. 1C, delay 50 enables a user to vary the position of noise 34 in scanned field 32, so that the noise is moved away from treatment site 38, to a different portion of scanned field 32. The user is thus provided a noise-free image of treatment site 38.

A HIFU duration circuit 52 is used to control the duration of the HIFU wave. A longer duration HIFU wave will apply more energy to the treatment site. Generally, the more energy that is applied to a treatment site, the faster a desired therapeutic effect will be achieved. However, it should be noted that if the HIFU wave is too long, the duration of noise 34 as shown in ultrasound image 30 will increase and can extend into the next ultrasound imaging pulse to obscure treatment site 28, or may completely obscure ultrasound image 30, generating a display very similar to ultrasound image 10 in FIG. 1A. Thus, the user will have to selectively adjust HIFU duration circuit 52 to obtain a noise-free image of treatment site 38, while providing a sufficient level of energy to the treatment site to effect the desired therapeutic effect in an acceptable time.

A HIFU excitation frequency generator 56 is used to generate the desired frequency for the HIFU wave, and a power amplifier 58 is used to amplify the signal produced by the HIFU excitation frequency generator to achieve the desired energy level of the HIFU wave; power amplifier 58 is thus adjustable to obtain a desired energy level for the HIFU wave. Optionally, a stable synchronization signal generator 66 can be used to synchronize the HIFU wave to the imaging ultrasonic wave, instead of using synchronization output signal 48 from ultrasound imaging machine 40. Stable synchronization signal generator 66 can be used to provide a stable synchronizing pulse to initiate the HIFU wave, and the timing of this stable synchronizing pulse can be selectively varied until a noise-free image of the treatment site has been obtained. A drawback of using stable synchronization signal generator 66 instead of synchronization output signal 48 is that any change in the timing of the ultrasound imaging pulses, such as is required to scan deeper within tissue, will require an adjustment to stable synchronization signal generator 66 that would not be required if synchronization output signal 48 were used. The processor will be able to automatically find a stable synchronization signal using information from the movement of the noise.

Figure 4:
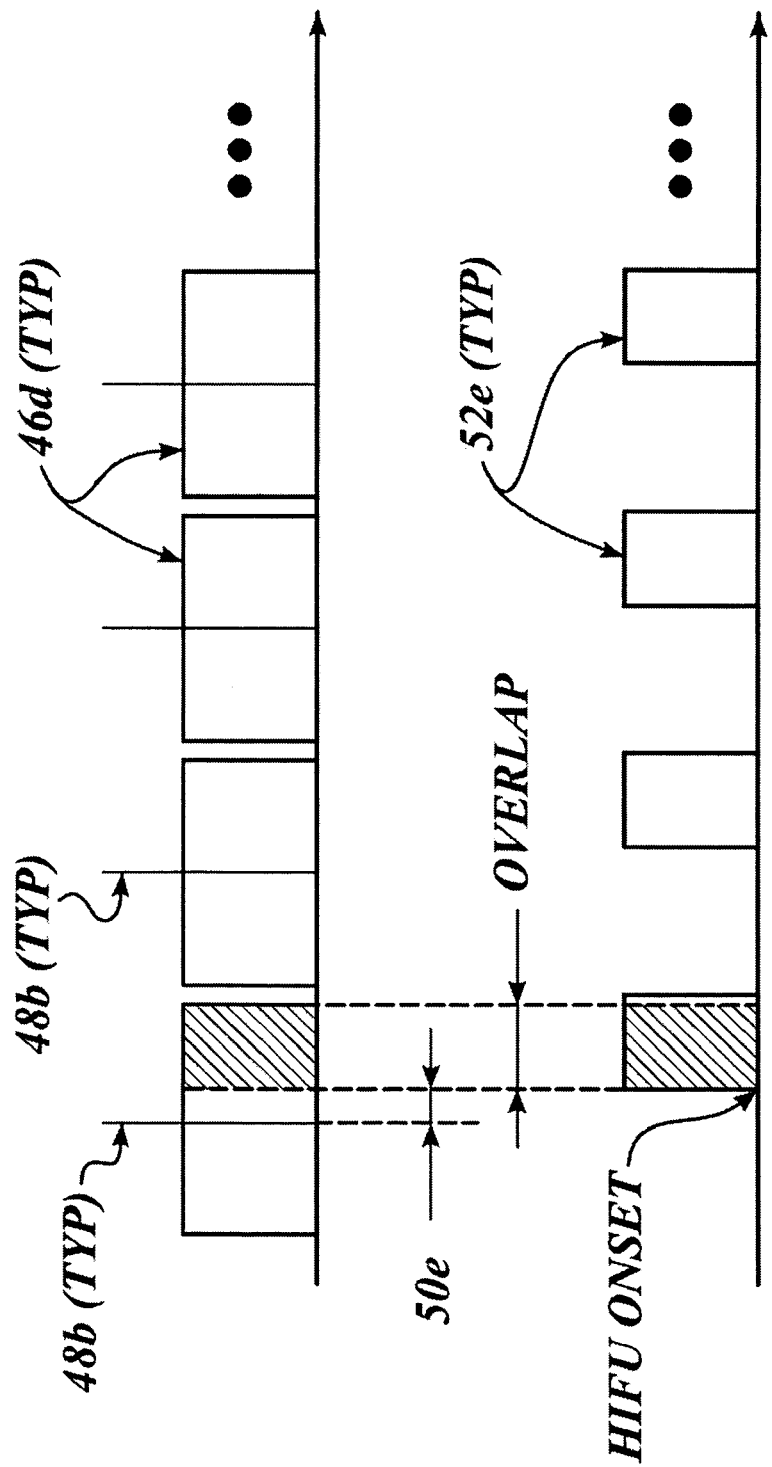

FIGS. 3A(1)-3D(4) and FIG. 4 provide further detail for the synchronization and pulsing features of the present invention. FIG. 3A(1) shows ultrasound imaging pulses 46a produced by imaging machine 40 and imaging probe 44 that are used to acquire an ultrasound image of a target area (such as ultrasound image 30 of FIG. 1C). A synchronization pulse 48a is shown in FIG. 3A(2). It should be noted that synchronization pulse 48a is illustrated as occurring before the generation of ultrasound imaging pulses 46a; however, the timing of synchronization pulse 48a relative to the imaging pulses is not critical, so long as it is stable. Synchronization pulse 48a merely establishes a timing reference point, from which a delay 50a (shown in FIG. 3A(3)), used for the initiation of the HIFU wave, is set such that noise from the HIFU wave in an ultrasonic image generated by imaging pulses 46a is shifted away from the image of the treatment site. The delay 50a is not fixed, and it is adjusted by the user until a noise-free image of the treatment site is obtained.

A HIFU duration 52a, shown in FIG. 3A(4), determines the duration of the HIFU wave. HIFU duration 52a may be very brief, as shown in FIG. 3A(4), or extended, as shown in FIGS. 3B(4) and 3C(4). An increase in the duration of the HIFU wave will cause a greater portion of an ultrasound image to be obscured by noise, and may cause the HIFU wave to interfere with the image of the treatment site. In FIG. 3A(4), delay 52a is very short, and the resulting noisy region in the ultrasound image will be very small. However, a short duration HIFU wave means a correspondingly small amount of HIFU energy will be delivered to the treatment site, thus increasing the length of the treatment. A clinician must balance the length of HIFU duration needed to maintain a noise-free image of the treatment site against the time required to complete the therapy. It should be noted that as an alternative to using HIFU duration 52a to control the HIFU excitation frequency generator to variably set the duration of the HIFU wave, the HIFU excitation frequency generator itself could be adjusted to control the duration.

FIGS. 3B(1)-3C(4) similarly illustrate timing patterns that incorporate different settings for the delay relating to the initiation of the HIFU wave (setting 50b in FIG. 3B(2), and setting 50c in FIG. 3C(2)) and delay relating to the duration of the HIFU wave (setting 52b in FIG. 3B(3), and setting 52c in FIG. 3C(3)). FIGS. 3D(1)-3D(4) illustrate a timing pattern that enables a longer duration HIFU wave (thus more energy applied to the treatment site) to be used, while still enabling a noise-free image of the treatment site to be generated. In FIG. 3D(1), ultrasound imaging pulses 46b and 46c appear to be much shorter than in FIGS. 3A(1), 3B(1) and 3C(1), but actually are of the same duration, as the scales of FIGS. 3D(1)-3D(4) have been significantly increased. Synchronization pulse 48a of FIG. 3D(2) is obtained and used as described above. A delay 50d in FIG. 3D(3) is set to obtain a noise-free image of the treatment site, also as described above; however, as will be clarified below, not all of these synchronization pulses govern the image that is produced, as the delay 52d dominates. The significant difference between FIGS. 3D(1)- 3D(4) and FIGS. 3A(1)-3C(4) is that delay 52d has been significantly increased in FIG. 3D, such that a very long burst of HIFU energy is emitted, almost to the point of continuous emission. Here, the noise-free imaging occurs only every seventh image, during interrogation wave 46c. By adjusting delay 52, more or fewer images will be interfered with, and therefore, various duty cycle lengths for HIFU exposure can be accommodated. It should be noted as the number of images interfered with by the HIFU wave increases (here, 6 out of 7), the resulting image of the target area will arguably provide less real-time feedback. However, the actual time between visible images of the treatment site may be so short as to appear to occur in real time. But, at very high settings for the HIFU duration (such as to cause the HIFU wave to interfere with 99 out of 100 images of the treatment site), the advantages associated with real-time imaging of the treatment site are diminished. Thus, the HIFU duration will preferably not be set so high as to negate the benefits of real-time imaging of the treatment site and its ability to provide the clinician with immediate feedback concerning the effect of the therapy on the treatment site.

FIG. 4 illustrates another timing sequence that shows the relationships between ultrasound imaging pulses 46d, a synchronization pulse 48b, a delay 50e, and a HIFU duration 52e. In this timing sequence, synchronization pulse 48b occurs during the ultrasound imaging pulses 46d, rather than preceding the ultrasound imaging pulses, as shown in FIGS. 3A-3D. As noted above, the position of each synchronization pulse 48b relative to the ultrasound imaging pulses is not critical, as delay 50e is adjusted to shift the noise away from the image of the treatment sight. Again, the duration of the HIFU wave (and thus, the energy applied to the treatment sight) is varied either by adjusting delay 52e, as shown in FIG. 4, or by adjusting the HIFU excitation generator.

Imaging of HIFU Focal Point

It will often be important for a clinician to be able to confirm that the focal point of a HIFU transducer is directed at a desired treatment site before initiating HIFU therapy. It has been determined that if the energy level of a HIFU transducer is reduced to a level less than a level that would cause any damage to tissue, the focal point of the HIFU transducer will still be evident within the target area displayed in the image developed from the reflected ultrasound signal produced and received by the ultrasound imaging transducer. The focal point will appear as a bright spot in the displayed image and will rapidly fade over time. Thus, it is possible for a clinician to move the HIFU transducer as necessary to shift the focal point to a desired treatment site in the target area being imaged by the ultrasound imaging transducer and to see the focal point in the image as a bright spot that moves as the position of the HIFU transducer is changed. Only after the focal point is positioned on a desired treatment site will the clinician increase the energy of the ultrasound pulses produced by the HIFU transducer to a level sufficient to achieve the desired therapeutic effect, e.g., to a level sufficient to necrose tissue, or cause hemostasis. It should be noted that the ultrasound imaging transducer is not receiving the ultrasound signal produced by the HIFU transducer that is reflected by the tissue, but instead, is likely imaging the effect of the change in echogenicity of the tissue caused by the relatively low energy ultrasound burst produced by the HIFU transducer. This technique can be used with any of the HIFU transducers discussed below.

A further advantage of the preceding technique for imaging the focal point of a HIFU transducer can be achieved by storing the image of each successive treatment site, which will appear as a bright area in the image produced by the ultrasound imaging transducer system. For example, a storage type display, of the type readily available, can be used for this purpose. By storing the image of each treatment site to which the HIFU therapy has previously been administered during a current session, it is possible for a clinician to target spaced-apart treatment sites in the target area, thereby ensuring the HIFU therapy has been administered to all of the desired portion of a tumor or other structure in the patient's body. Since each previous treatment site will be visible in the image, it will be apparent that a desired pattern of treatment sites can readily be laid down over the tumor or other structure of interest. The change in echogenicity caused by a relatively high energy therapeutic HIFU wave will be brighter and persist longer in the display, enabling the clinician to easily distinguish between a current prospective focus point for the next treatment site (produced using the low energy pulse), and the previous treatment sites to which the HIFU therapy has already been administered.

3D Imaging System

In FIG. 22, a block diagram is illustrated for a system 200 that enables imaging of a target area in 3D and storing of the locations of treatment sites to which the HIFU therapy has been administered in the 3D image as a HIFU therapy session proceeds. The system includes a 3D image data processor and display 202, an image acquisition section 204, a magnetic field sensor 206, a magnetic field generator 208, and 6D electronic processing circuitry 210. The latter three components are employed to track the imaging target area and the HIFU focal point as they are redirected in the 3D space and are part of a six-dimensional (6D) measurement system (i.e., three spatial coordinates for the 3D orthogonal axes and three angles of rotation around these three orthogonal axes). A 6D measurement system is commercially available from Ascension Technology, Burlington, Vt. This 6D measurement system uses 6D electronic processing circuitry 210 and magnetic field generator 206 to produce time sequential orthogonally oriented magnetic fields covering a general area as indicated in the Figure by the dash line that encompasses the region of magnetic field. Magnetic field sensor 206 is mounted on a combined imaging and HIFU therapy probe 212 in a fixed manner relative to imaging and HIFU transducers 214. The magnetic field sensor detects the magnetic field strength in 3D sequentially produced by the magnetic field generator. The 6D electronic processing circuitry uses the information from the magnetic field sensor and the known magnetic fields that were produced to compute the 3D position and the three angular orientations around the three orthogonal axes of the magnetic field sensor (and thus, of the combined imaging and HIFU therapy probe) with respect to the magnetic field generator, yielding the 6D information. The 6D information is supplied to 3D image data processor and display 202 at a rate sufficient to enable movement of the magnetic field sensor to be tracked in the displayed 3D image of the target area. With information derived from calibrating system 200 with the imaging probe, the position of the target area and the HIFU transducer focal point can be related to a 3D spatial point, so long as magnetic field sensor 206 is within the range of the magnetic field produced by magnetic field generator 208. 3D image data processor and display 202 also receive ultrasound image information from an ultrasound imaging machine 216 through image acquisition section 204. It uses this information to develop and display 3D information. Ultrasound imaging machine 216 provide the synchronization signal to a HIFU control and electrical energy generating system 218, as discussed above. The remaining component in FIG. 22 is a physiological information acquisition section 220, which enables synchronization of the imaging and HIFU therapy with physiological activity, such as respiration or cardiac activity (provided by an electrocardiogram system—not shown). Use of the physiological information avoids problems associated with movement of the patient's body due to physiological activity. For example, 3D imaging and HIFU therapy can be control so that they are implemented only at the end of expiration in the breathing cycle, since motion of the patient is more repeatable then than at mid inspiration. A physiological sensor such as a respiration detector (not shown), which is well known in the art, can provide the information for this section of the system.

As noted above, by storing the location of each of the treatment sites where HIFU therapy has been administered during a therapy session, a clinician will be able to determine where each successive treatment site should be targeted to achieve a desired pattern of HIFU therapy within a tumor or other region of interest. The bright spot in the 3D image showing the location of each previous treatment site greatly facilitates this targeting process and enables a desired pattern of HIFU therapy to be achieved with considerable accuracy.

By using the 3D display to view the progression of successive treatment sites, other types of therapeutic results can be achieved. For example, the HIFU therapy can be employed to create a plurality of lesions on blood vessels supplying blood to a tumor, cutting off the supply of nutrients and oxygen to the tumor provided by the blood supply. Thus, it is possible to destroy a tumor without directly using the HIFU therapy to destroy tumor tissue. The results of this technique are similar to those arising from the procedure referred to as "embolization," in which a clot-inducing material is introduced into the vessel using a small catheter, but the HIFU therapy can achieve the same result non-invasively and can treat vessels that are too small or otherwise not accessible to render treatment through a catheter. Embolization is a relatively new technique and has been used to treat a variety of conditions, including uterine fibroids. While the ability to store the location of previous treatment sites so that they are shown on a displayed 3D image of the target area is not essential to this use of HIFU therapy, it will be evident that the display of the treatment sites used to create lesions in the vessels will facilitate this procedure. Further, it should be noted that using HIFU to occlude (or induce hemostasis in) the blood vessels that supply oxygen and nourishment to a structure within the body can be used in conjunction with other imaging techniques, such as CT, MRI, or angiography.

Another imaging technique that is likely to be useful to a clinician when using HIFU to create lesions in blood vessels is Doppler Flow imaging, which can be used to represent blood vessels supplying a structure with blood in one color, and blood vessels that remove blood from a structure in a second color. As those of ordinary skill in the art will readily recognize, the circulation of blood within these blood vessels either adds to or subtracts from the imaging wave, enabling blood vessels having blood flowing in opposite directions to be differentiated from one another.

A final imaging technique that will likely be beneficially employed by a clinician using HIFU to create a lesion in a blood vessel is the use of conventional ultrasound imaging contrast agents. Not only will the use of such agents provide the clinician with a more useful ultrasonic image, but the use of such agents will increase the effectiveness of the HIFU in producing the desired lesion. The use of contrast agents is discussed in greater detail below.

Advantage of Simultaneous, Real-Time Imaging

Major advantages to real-time imaging of therapeutic HIFU while it is being applied are: (1) the HIFU treatment can be stopped when a therapeutic produced lesion has grown to the point at which it begins to extend beyond the desired treatment site, and the HIFU focal point can then be repositioned to another treatment site and reactivated; (2) the focal point of the HIFU wave can be observed in the image due to changes in the echogenicity of the tissue at the focal point, which are apparent in the images of the target area, providing an instant feedback that can enable a clinician to adjust the focal point onto a desired treatment site; (3) the HIFU focal point can be adjusted during the administration of the HIFU therapy to compensate for tissue movement within the patient's body due to breathing or for other reasons; (4) real-time visualization of a treatment site is very reassuring to the medical therapist, in confirming that the HIFU energy is being applied to the correct position (and that healthy tissue is not being damaged); (5) the combined imaging and therapeutic treatment can be accomplished much faster than in the past, when it was necessary to render treatment, stop the treatment, image the site, and then continue the treatment; and, (6) it enables the clinician to administer the HIFU therapy in a desired pattern of treatment sites so that, for example, a matrix of necrotic points in a tumor can be achieved to de-bulk the tumor without treating all of the tumor. Further details of how each of these advantages are achieved by the present invention are discussed below.

Figure 5A:
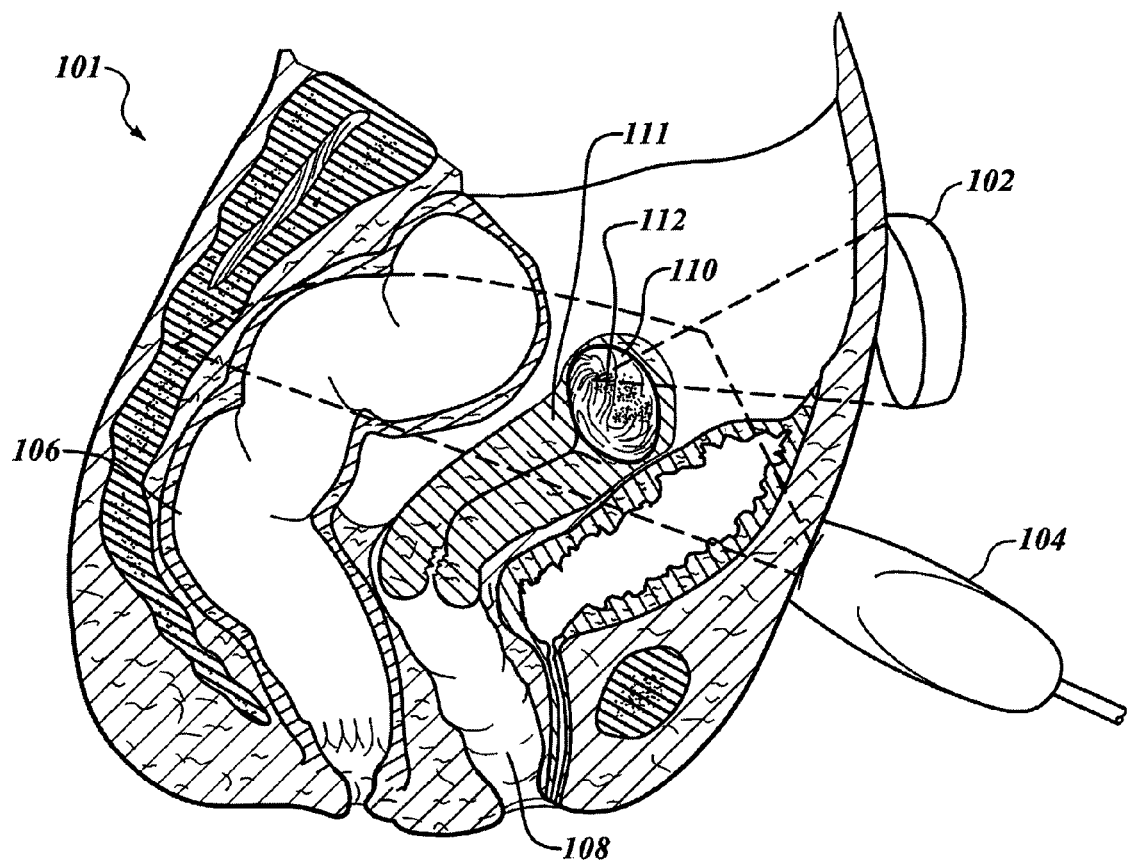
Figure 5B:
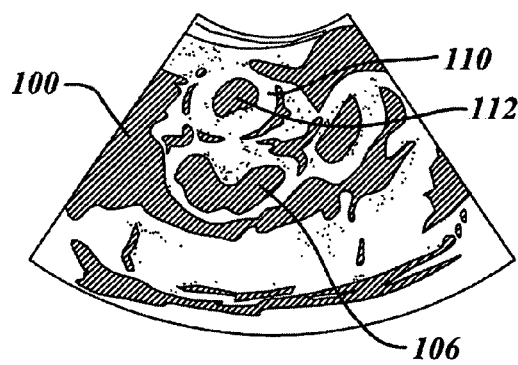
Figure 6:
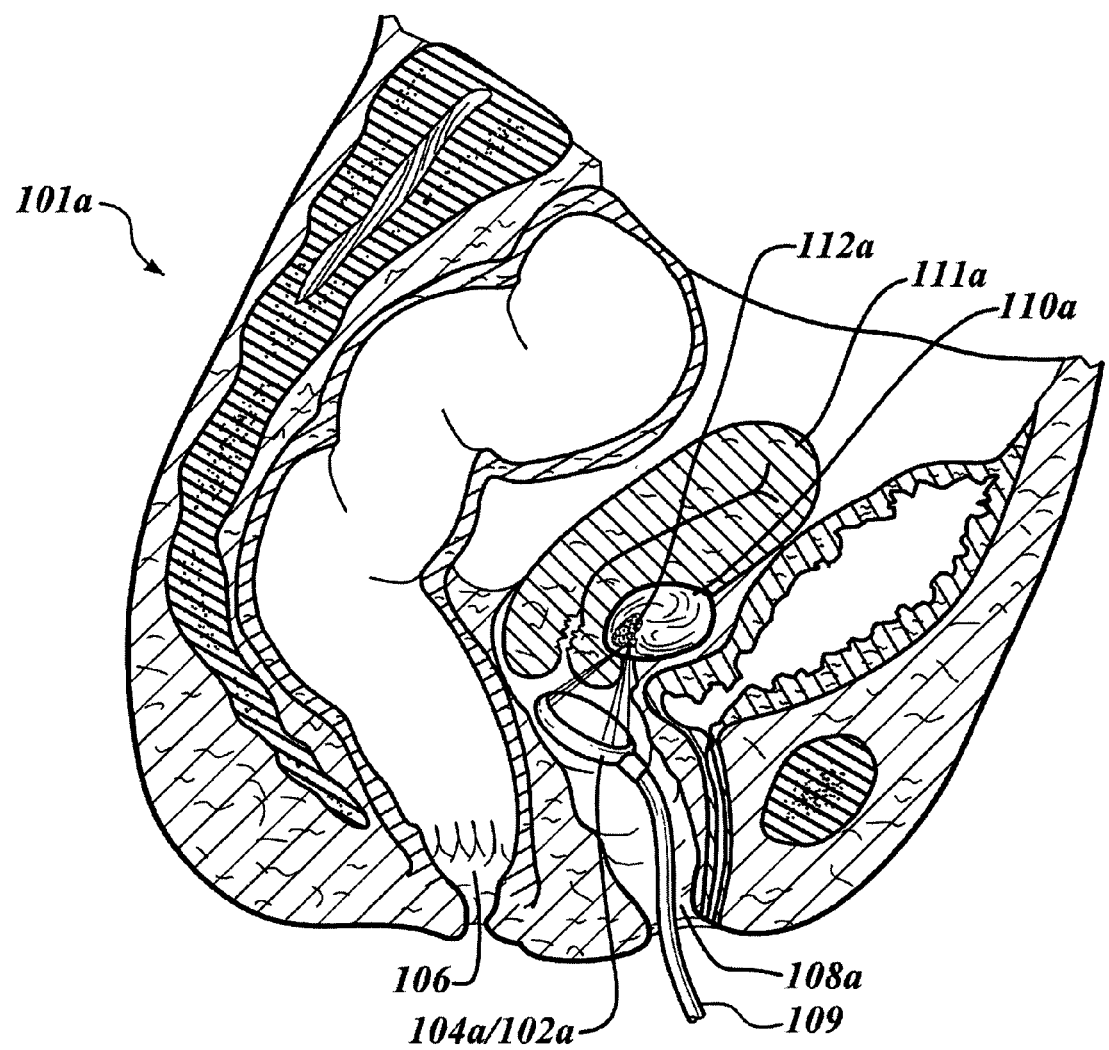
FIG. 6 is a schematic view of a vaginal probe that includes both imaging and therapeutic ultrasonic transducers being used for the simultaneous imaging and treatment of a tumor in a female reproductive system.
Figure 7:
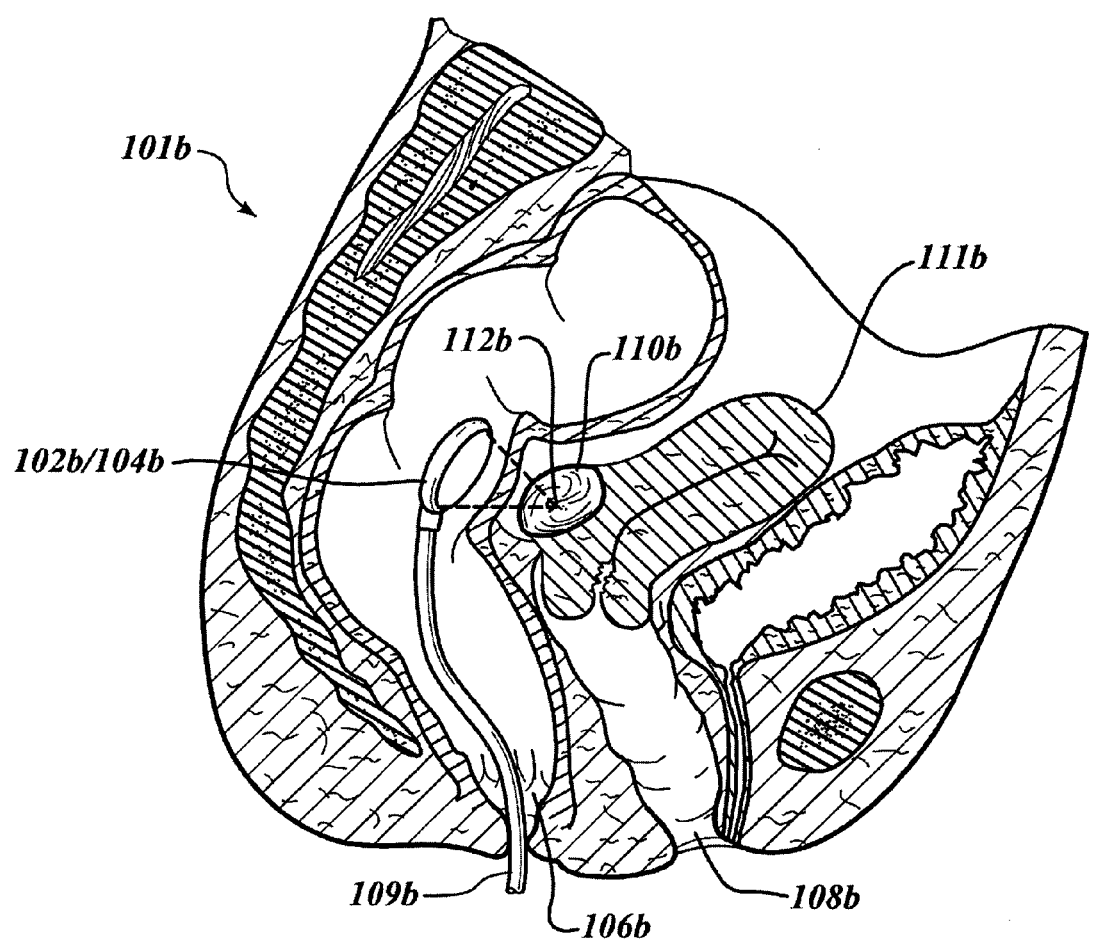
FIG. 7 is a schematic view of a rectal probe that includes both imaging and therapeutic ultrasonic transducers being used for the simultaneous imaging and treatment of a tumor in a female reproductive system, where the HIFU beam passes through the rectal wall into the uterine cavity.

FIGS. 5-7 illustrate how a variety of different configurations of HIFU transducers and imaging transducers can be used to simultaneously provide real-time imaging and therapy to an internal treatment site within a patient's body. It is expected that HIFU therapy with real-time imaging can be beneficially employed to treat a variety of disease conditions. In particular, it is envisioned that conditions relating to the reproductive system of a mammalian female will particularly benefit from HIFU therapy with real-time imaging, as ultrasonic imaging itself is widely used in association with the female reproductive system. It is envisioned that HIFU therapy can be applied to a uterine fibroid, an endometrial polyp, a follicular cyst, a polycystic ovary, a dermoid cyst, a corpus luteum cyst, an ectopic pregnancy, a cornual pregnancy, a multifetal pregnancy, a uterine malformation, an endometrial hyperplasia, an adenomyosis condition, and endometriosis condition, or an excessive bleeding condition. The treatment of disorders of the female reproductive system using the method of the present invention can be achieved by positioning the scanning ultrasonic transducer system and the therapeutic ultrasonic transducer system adjacent to the female reproductive system. Vaginal, rectal, abdominal and laparoscopic approaches are contemplated.

In FIG. 5, both a HIFU transducer 102 and an imaging transducer 104 are disposed external to the patient's body. The reflected ultrasound waves received by imaging transducer 104 are used to generate an ultrasound image 100. In FIG. 5, the HIFU is being used to treat a tumor 110 on a uterus 111 of the patient. Imaging transducer 104 is positioned so that tumor 110 is clearly displayed in ultrasound image 100. Also visible in ultrasound image 100 is a cross section of a rectum 106. HIFU transducer 102 is being used to destroy tissue in tumor 110. The necrotic tissue is clearly visible as a lesion 112 in both the cross section of the body and in ultrasound image 100.

FIG. 6 illustrates an embodiment in which a HIFU transducer 102*a* and an imaging transducer 104*a* have been combined on a vaginal probe 109. Vaginal probe 109 has been inserted into a vaginal canal 108*a* and positioned to enable imaging transducer 104*a* to be used in generating an ultrasonic image of a tumor 110*a*. Once tumor 110*a* has been located, HIFU transducer 102*a* is focused on a selected portion of tumor 110*a* to which the clinician desires to administer the HIFU therapy to generate a lesion 112*a*. The HIFU therapy is used to destroy the tumor by causing lesions of the blood vessels supplying oxygen and nutrients to the tumor, thereby generating a plurality of lesions similar to lesion 112*a*, so that the tumor withers away, or by destroying spaced-apart portions of the tumor. Particularly if the latter technique is used, the HIFU therapy will likely be repeated at intervals of several weeks. The time between successive therapy sessions enables macrophages in the patient's body to clear away or debride the necrotic tissue from the tumor so that it is reduced in size with each therapy session and eventually destroyed.

FIG. 7 illustrates a rectal probe 109*a*, which incorporates a combination of a therapy transducer 102*b* and an imaging transducer 104*b*. Rectal probe 109*a* has been inserted into a rectum 106*b* of the patient, and the imaging transducer is being used to locate a tumor 110*b*. Once tumor 110*b* has been located, therapy transducer 102*b* is focused on the desired portion of the tumor, and HIFU therapy is administered to a treatment site 112*b*, until the desired therapeutic effect is achieved. Note that tumor 110*b* is in uterus 111, and the HIFU beam passes through the rectal wall into the uterine cavity.

FIGS. 9-19 provide details of preferred embodiments of probes that can be used to simultaneously provide imaging and therapy to a treatment site. It should be noted that the method of simultaneously imaging and providing treatment using ultrasound can be applied to different locations in or on a patient's body to treat a variety of medical conditions. One application of a preferred embodiment of the present invention is employed, by way of example, to provided simultaneous ultrasonic imaging and HIFU therapy of a uterine fibroid. However, it should be understood that the simultaneous imaging and therapy using the described method is not at all limited to the treatment of uterine fibroids, or even the treatment of gynecological or obstetrical disorders.

Figure 8:
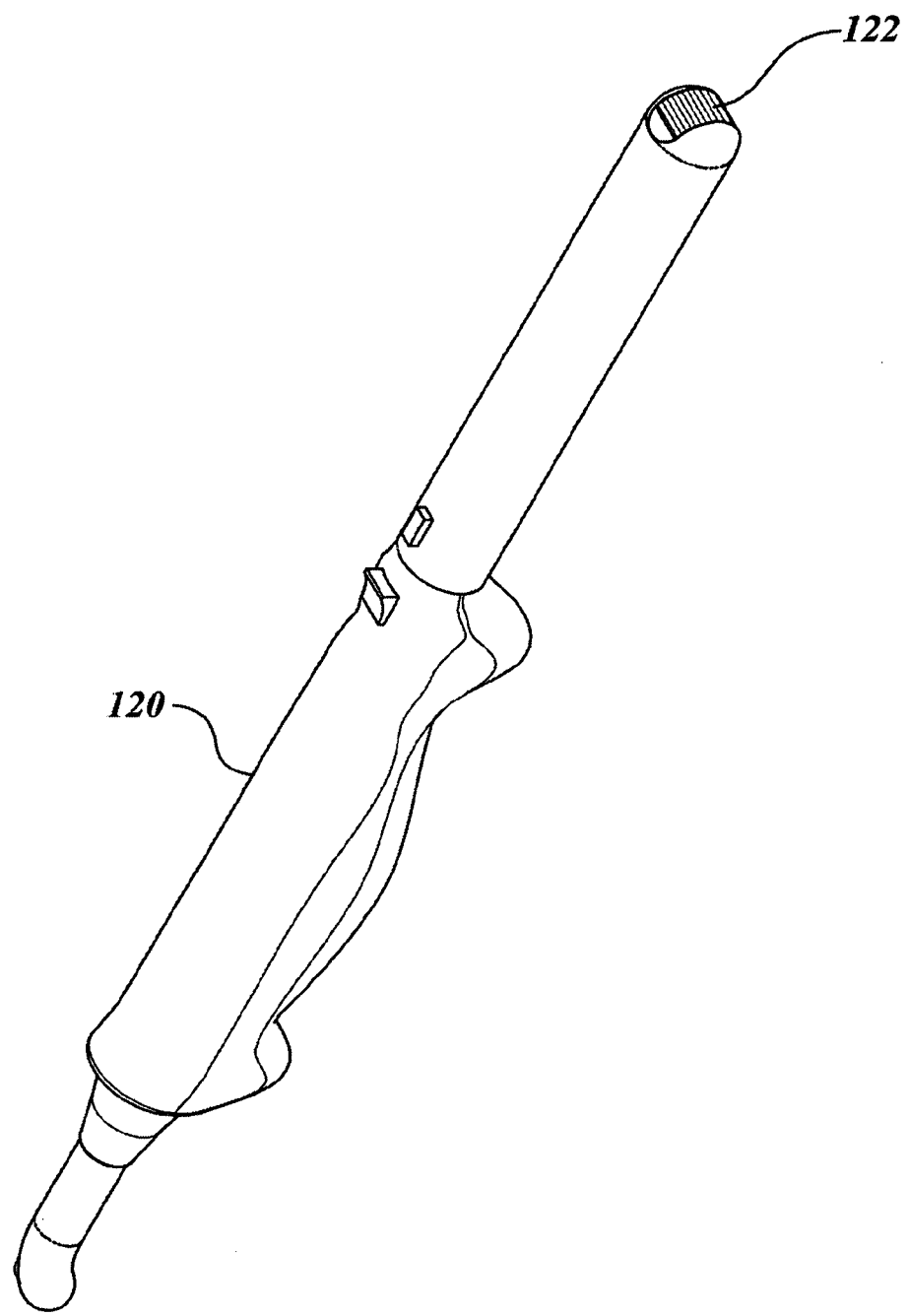
FIG. 8 (Prior Art) is a schematic view of a vaginal probe that includes an imaging transducer.

For an exemplary application of the present invention described below, a vaginal ultrasonic imaging probe is employed. Vaginal ultrasonic imaging probes are well known in the prior art. FIG. 8 illustrates one such prior art ultrasonic vaginal imaging probe, which is a Model C9-5 transvaginal probe available from ATL Inc. of Bothell, Wash. It is envisioned that several different types of HIFU transducers can be mounted onto the standard transvaginal imaging transducer probe to allow the simultaneous imaging and therapy of treatment sites related to the female reproductive system, in accord with the present invention.

Transducer and Probe for Vaginal Application of HIFU to Treat Uterine Fibroids As noted above, an exemplary application of the present invention is a vaginal probe incorporating both imaging and therapeutic transducers. As HIFU transducer design is a function of the location of the desired treatment site, the following discussion is useful in determining preferred design parameters for a vaginal probe combining imaging and therapeutic transducers optimized for applying HIFU therapy to uterine fibroids.

The relationship between the distance from the HIFU transducer to the focus (focal length) and the surface area of the aperture is well known to those of ordinary skill in the art. For a circular aperture, the f# (or relative aperture) is defined as being equal to the "focal length divided by the diameter of the aperture". A low number is preferred, as this insures a highly focused beam, thereby minimizing any undesired effects of the HIFU beam on adjacent tissue. A preferred number is 1; but a number as high as 1.75 can be used, therefore a practical range is from 1-1.75. The lower the number, the tighter the focus, and the greater the intensity of the HIFU beam will be at the focus, with respect to the HIFU beam intensity at the surface of the transducer. This is important because a high intensity is required at the focal point to achieve a desired therapeutic effect in a short period of time. Conversely, moderate or low intensities are needed at the surface of the transducer, so that the HIFU beam generated at the surface of the transducer can pass through the tissue intermediate to the transducer surface and the focal point. This intermediate tissue is affected by the at this point unfocused HIFU beam as it passes through the intermediate tissue to the focal point. If the unfocused HIFU beam is of sufficiently low intensity, the effect of the unfocused HIFU beam on the intermediate tissue will be negligible. As the unfocused HIFU beam approaches the focal point, the intensity increases as the HIFU beam becomes more focused, until a sufficient intensity is obtained at the focal point to achieve a desired therapeutic effect. Generally, the effect a HIFU beam has on tissue is to heat the tissue (though HIFU can also have a mechanical effect on tissue via cavitation). Therefore a low intensity at the surface of the transducer is desired to minimize the heating of the intermediate tissue, while for successful treatment, the tissue at the focus must be heated much more rapidly in order to achieve therapeutic temperatures at the focus without undue heat build up in the intermediate tissue. Therefore, it is very important to know the maximum distance from the transducer that one desires to treat, to determine the maximum focal length required. At the same time, one must have an understanding of the largest size aperture that one can physically introduce into the vaginal tract.

Based on a review of obstetrical and gynecological literature, the applicants experience, and a study of duckbill speculums (medical devices used for the inspection of the vagina and cervix.), applicants have identified that the external opening of the vaginal canal generally has a circumferential dimension which ranges from of 10-12 cm. Since the vaginal entrance is longitudinal in nature, a probe having a distal end that is "paddle" or "spoon" shaped would be most beneficially employed. Practical transducer considerations require that the distal end of the probe (the logical point for mounting a therapeutic transducer) would be at least 0.5 cm thick, and that the widest portion of this "paddle" design would range from 4.5-5.5 cm. Since the vagina is a muscular structure that is quite strong, it can be stretched somewhat further, but this is uncomfortable for the patient. Therefore, it is preferred that the widest portion of the paddle range from 4.5-6 cm.

The design of a preferred focal length necessitated an analysis of where within the vaginal canal the probe will be positioned, and where uterine fibroids are likely to occur. Preferably the probe will be positionable in the vagina at the cervix. The vaginal fornices are potential spaces formed by folds within the vaginal canal around the cervix, extending 5-6 cm along the uterus. Therefore, near the cervix, the vaginal cavity has a larger space, allowing either a larger probe, or the manipulation of a smaller probe, to achieve imaging and therapy of a desired site in the uterus. Based on a review of obstetrical and gynecological literature, the size range of uterine fibroids is from 1-15 cm, and the length of the uterus is approximately 5-6 cm. Therefore, a maximum focal length of about 20 cm would reach an entire fibroid located at the distal end of the uterus. Based on applicants' practical experience, it is anticipated that 20%, 35%, 50%, 75%, and 80% of all uterine fibroids will be within the respective distances of 4 cm, 6 cm, 8 cm, 10 cm and 12 cm respectively. From a cost/benefit point of view, a combination imaging and therapeutic vaginal probe needs to be able to treat at least 35% of uterine fibroids, and more preferably 50%. Therefore a preferred therapeutic transducer must be able to treat to a depth of at least 6 cm, and more preferably 8 cm.

The design of different embodiments of a vaginal probe including both imaging and therapeutic transducers is preferably limited to designs in which the largest circumferential dimension of the combination probe (measured generally transverse to a longitudinal axis of the probe) is about 10.6 cm, which is a nominal limit in size to enable the combination imaging and therapy transducer to be readily inserted through the vaginal opening and into the vaginal canal.

TABLE 1

Percentage of Fibroids Treatable for Relative Apertures with an area equivalent to a Circular Aperture

| Circular Aperture Diameter (cm) | Relative Apertures (f#) | | |
| --- | --- | --- | --- |
| | 1.25 | 1.5 | 1.75 |
| 4.5 | <35% | >35% | 50% |
| 5 | 35% | <50% | <75% |
| 5.5 | <50% | 50% | <75% |
| 6 | <50% | <75% | 75% |
| 6.5 | 50% | <75% | <80% |
| 7 | <75% | 75% | 80% |
| 7.5 | <75% | <80% | |
| 8 | <75% | 80% | |
| 8.5 | 75% | | |
| 9 | <80% | | |
| 9.5 | 80% | | |

Based on the calculations for a circular aperture and practical relative apertures, Table 1 provides information of the relative percentages of uterine fibroids that can be treated with a specific circular aperture. For a circular aperture of 4.5 cm, just less than 35% of all uterine fibroids can be treated with a relative aperture of 1.25. This then defines the minimum diameter of circular applicator as 4.5 cm, based on the design parameter of being able to treat 35% of uterine fibroids encountered. An elliptic aperture may also be used, in which case the minor axis represents the transverse direction, and thus the limiting dimension of a probe that can readily be inserted into the vagina. An elliptical surface area is larger than a circular surface if the minor axis length equals the diameter of the circular surface, and the major axis is greater than the minor axis. By using an elliptical surface, the focal length is greater than for a circular surface for a given relative aperture number. Therefore, with a two to one ratio of major to minor axis for example, a 9/4.5 ratio would exist for the minor axis chosen. Referring to Table 2, this is equivalent to a 6.5 cm diameter circular aperture. Looking at Table 1, for the equivalent of a 6.5 cm diameter circular aperture, the percentage of fibroids that can be treated are 50%, <75%, and 75%, respectively, for relative apertures of 1.25, 1.5, and 1.75.

These results therefore dictate a vaginal probe with a HIFU transducer that has a distal end that is paddle or spoon shaped, with a minimum transverse dimension of 4.5 cm, and a maximum circumferential dimension (measured generally transverse to a longitudinal axis of the probe) of about 10.6 cm. No other devices cited in the prior art for use in other body orifices are suitable for a vaginal application of HIFU for the treatment of uterine fibroids. The size, shape, and configuration of such a combination imaging and therapy vaginal probe are believed to be specific to this particular access path through the vaginal canal, for rendering the HIFU therapy in treating obstetrical and gynecological medical conditions.

TABLE 2

Major axis length (cm) for a given a minor axis length that gives an ellipsoidal area equal to the area of a circular aperture of a specific diameter.

| Diameter Circular Aperture | Ellipsoid Minor Axis Length (cm) | | | |
|---|---|---|---|---|
| | 4.5 | 5 | 5.5 | 6 |
| 4.5 | 4.5 | 4.1 | 3.7 | 3.4 |
| 5 | 5.6 | 5.0 | 4.5 | 4.2 |
| 5.5 | 6.7 | 6.1 | 5.5 | 5.0 |
| 6 | 8.0 | 7.2 | 6.5 | 6.0 |
| 6.5 | 9.4 | 8.5 | 7.7 | 7.0 |
| 7 | 10.9 | 9.8 | 8.9 | 8.2 |
| 7.5 | 12.5 | 11.3 | 10.2 | 9.4 |
| 8 | 14.2 | 12.8 | 11.6 | 10.7 |
| 8.5 | 16.1 | 14.5 | 13.1 | 12.0 |
| 9 | 18.0 | 16.2 | 14.7 | 13.5 |
| 9.5 | 20.1 | 18.1 | 16.4 | 15.0 |

FIG. 9 illustrates a first embodiment for mounting a HIFU module 123 onto a distal end of a prior art transvaginal imaging probe 120. Transvaginal imaging probe 120 includes an imaging transducer array 122. HIFU module 123 is sized and shaped to fit over the distal end of transvaginal imaging probe 120 and incorporates a cylindrical shaft 124 that has a cylindrical bore 126. Cylindrical bore 126 is sized to easily slide over the distal end of transvaginal imaging probe 120 and in its wall is disposed a plurality of fluid passages 130. Those of ordinary skill in the art will readily understand that ultrasonic waves do not readily pass through air gaps, and water or other fluid filled balloons are often used to conduct an ultrasonic wave between the ultrasonic transducer from which it is transmitted and a target of interest. Fluid passages 130 are used to circulate degassed water through a balloon 140 (FIG. 10) that surrounds HIFU module 123. It is important that the water be degassed, as bubbles within the water increase cavitational effects, which will attenuate the ultrasonic waves. The water circulating through the balloon provides cooling to the transducer elements to avoid an unwanted buildup of heat. It is currently common practice to use a condom for a balloon, although other inert and flexible elastomeric materials could be used.

In FIG. 10, vaginal probe 120 has been inserted into cylindrical bore 126 of cylinder 124, and the imaging transducer array 122 is disposed within a void 138. Shaft 124 also includes electrical leads 128, which connect the HIFU transducer to the power amplifier that drives the HIFU transducer. Located atop cylinder 124 is a HIFU transducer mounting base 136. It should be noted that HIFU transducer mounting base 136 is also hollow, such that the transvaginal imaging probe 130 may pass completely through the center of HIFU transducer mounting base 136 so that imaging transducer array 122 is disposed within void 138 (see FIG. 9B). This configuration enables imaging transducer array 122 to transmit an ultrasound imaging pulse to the target of interest.

As shown in FIG. 10, HIFU therapy transducer 132 is pivotally mounted to HIFU transducer mounting base 136 at a pivot joint 134. This pivotal mounting enables a clinician to selectively target a wider variety of treatment areas within the female reproductive system by rotating the HIFU transducer about pivot joint 134. It is envisioned that the disposition of the HIFU transducer on pivotal mounting 134 will be adjusted prior to inserting the combination transvaginal probe and HIFU module into the vaginal canal. The angle of the HIFU transducer should be adjusted based on the relative position of the target area and treatment site. Once in the vaginal canal, the combination transvaginal imaging probe and HIFU module can be moved to a position that enables an ultrasonic image of the target area to be observed on a display and then adjusted to focus the HIFU wave onto a desired treatment site within the target area.

It is envisioned that a mechanical linkage (not shown) connected to HIFU transducer 132 can be added to enable the HIFU transducer to be selectively rotated about pivot joint 134 while the combination transvaginal probe and HIFU module is in the vaginal canal. This capability would provide a clinician greater flexibility in focusing the HIFU transducer on a particular treatment site. However, it should be noted that a skilled clinician can initially select an angle for the HIFU transducer relative to the longitudinal axis of the transvaginal imaging probe, insert the combination vaginal probe and HIFU module into the vaginal canal, and then manipulate the combination imaging probe and HIFU module while in the vaginal canal to acquire the image of the target area and focus the HIFU beam on the desired treatment site.

FIG. 11 illustrates an ultrasonic image 142 superimposed on the combination transvaginal probe and HIFU transducer illustrated in FIG. 10 (but without balloon 140). In FIG. 11, the HIFU transducer 132 has been focused on a treatment site 144. The synchronization and pulsating elements described earlier have been used to shift a noise section 146 away from treatment site 144, such that the clinician is provided with a noise-free real-time image of treatment site 144.

FIG. 12 illustrates another embodiment of a combination imaging and therapy transducer based on a prior art transvaginal imaging probe. A therapy transducer module 150 has been mounted onto transvaginal imaging probe 120. The design of the module is constrained by the anatomy involved in the transvaginal application of HIFU to uterine fibroids, as discussed above. Module 150 is mounted at the tip of the vaginal probe, and contains an opening through which the scan head (imaging transducer) transmits an ultrasound wave to obtain an image of the uterus, the fibroid, and any other structure of interest. The opening allows about one half of the scan head to transmit the imaging ultrasound wave. The other half is covered by the module assembly, and does not have a window for imaging, and therefore does not contribute to the image. In other words, half of the ultrasound image obtained by the vaginal probe in this configuration is masked by the assembly and is blank. The main housing of the module is made of biocompatible, medical grade plastic. A chamber 158 can be filled with a fluid, such as degassed water, for the purpose of coupling the HIFU to adjacent tissue. A water circulation system is used to circulate degassed cold water through chamber 158 for both cooling of the HIFU transducer and carrying away any cavitation bubbles that may be generated during the HIFU excitation. The water conduits extend through the plastic housing and two holes disposed on opposite sides of a central passage (not shown). Stainless steel needle stock can be employed for tubes 155 carrying the water in and out of the chamber. Tubes 155 run along the shaft of the vaginal probe adjacent to a coaxial cable 153 employed for energizing the HIFU transducer. A cover 159 attaches the membrane which forms chamber 158 to module 150.

Further details of therapy transducer module 150 are provided in FIG. 13. A HIFU transducer 154 is disposed on a rim cut inside a brass bowl 152 that is affixed with an appropriate adhesive to module 150. An electrical connection to the HIFU transducer is made through coaxial cable 153 that runs along the shaft of the probe. Preferably, the HIFU transducer is a concave, fixed focused transducer, operating at a center frequency of about 2.0 MHz. The radius of curvature of this embodiment of the HIFU transducer is about 55 mm, and its aperture diameter is about 35 mm. The focus of the HIFU transducer is within the imaging plane of the imaging probe (preferably an ATL, Inc., Model C9-5 transvaginal probe). In fact, the imaging plane intersects the HIFU beam envelope (cone shaped) through its center, placing both the focus and the HIFU beam longitudinal axis in the imaging plane, as can be seen in FIG. 14.

The HIFU transducer frequency was selected based on several requirements, including: (1) the ability to administer HIFU therapy to uterine fibroids up to a maximum distance of about 6 cm from the cervix; and, (2) an intensity gain of about 20 dB from the transducer surface to the focal spot, providing about 1,000 W/cm$^2$ at the focus, and about 50 W/cm$^2$ at the transducer surface. These are all reasonable values for both treatment and transducer operation. Two different embodiments of chambers containing degassed water are contemplated for the purpose of coupling the HIFU to adjacent tissue. These embodiments include a chamber containing just the HIFU transducer, and a chamber containing both the HIFU transducer and the imaging scan head.

FIG. 14 illustrates a combination transvaginal probe and HIFU transducer with both the imaging and HIFU transducer energized and chamber 158 filled with fluid. The HIFU transducer produces a cone-shaped HIFU wave 162 that is focused at a focal point 166. The imaging transducer generates a scanning ultrasound wave 160. It should be noted that HIFU wave 162 is within scanning wave 160. Thus, focal point 166 can be readily seen in the image provided by scanning ultrasound wave 160.

FIG. 15 illustrates an alternative design of a therapy transducer module 170 mounted on transvaginal imaging probe 120. As in the previous embodiment, imaging transducer array 122 is partially occluded by module 170, and thus only a partial ultrasound image is generated. A HIFU therapy transducer 174 is mounted on a brass ring 178, in a manner similar to the configuration in the previous embodiment. A fluid filled chamber 158a encloses HIFU therapy transducer 174. The most significant difference between the embodiment illustrated in FIG. 15 and the embodiments illustrated in FIGS. 13 and 14 is that fluid filled chamber 158a of FIG. 15 only encloses HIFU therapy transducer 174, and not imaging transducer array 122 as well.

FIGS. 16 and 17 illustrate an embodiment of probe usable in the present invention in which the HIFU therapy transducer and imaging transducer have been integrated into a single device. It is anticipated that as the combination of real-time imaging and HIFU therapy gains acceptance, clinicians will desire an integrated device rather than a HIFU transducer and a imaging transducer configured as two separate components, mounted together on a single probe. An integrated imaging transducer and a therapy transducer are formed as a combination transvaginal probe 180 as shown in these Figures. FIG. 17 illustrates that the angle of a paddle head 186 containing both the therapy and imaging transducers is movable relative to the body of combination transvaginal probe 180. As was discussed in regard to the first embodiment of the transducer module that included the pivoting HIFU transducer, it is expected that paddle head 186 will be placed in a desired position prior to placing combination transvaginal probe 180 into a patient's vaginal canal. However, it is again envisioned that a linkage mechanism can be incorporated that will enable paddle head 186 to be moved relative to the handle portion of combination transvaginal probe 180, while the paddle head is disposed in the vaginal canal. As noted earlier, the paddle head configuration is particularly well suited for use in the vaginal canal.

FIGS. 18 and 19 illustrates the paddle head probe with imaging transducers 182 and 182a positioned at two different angles relative to the longitudinal axis of the paddle head. In FIG. 18, imaging transducer 182 is generally parallel to the axis, while in FIG. 19, an imaging transducer 182a forms an angle of 90° relative to the axis. Those of ordinary skill in the art will recognize that the spatial orientation of the imaging transducer determines the plane of the scanning field. It should be noted that imaging transducers 182 and 182a comprise a one-dimensional (1D) phased array of transducer elements, and a linear array concentric ring HIFU transducer 184 is provided. Those of ordinary skill in the art will readily understand that the 1D phased array imaging transducers allow the ultrasound waves that are generated thereby to be steered and focused through a substantial range in a plane, while the concentric phased array of the HIFU transducer can only be electronically focused at different points along its central axis. The probe can thus remain stationary while the scanning ultrasonic wave are steered and/or focused at a target area and the HIFU waves are focused on a treatment site within the target area.

Also shown in FIG. 19 is a vibrating element 190. When activated, vibrating element 190 causes the focal point of the therapeutic ultrasonic wave to be varied, thus enlarging the size of the treated area within a limited portion of the target area without requiring the clinician to move the probe. Preferably, the clinician can select from two vibrational patterns; a first pattern that involves a vibrational frequency in the range of 1 to 5 Hz (thereby avoiding the heating of tissue not associated with the treatment site), and a second pattern that involves a vibrational frequency in the range of 10 to 50 Hz (thereby increasing an amount of energy applied to the treatment site, while avoiding undesired cavitational effects). While a specific type of vibrating element is not required, it is envisioned that readily available electromechanical vibrating elements will be employed for this purpose. It should be noted that vibrating element 190 could be beneficially incorporated into other probe embodiments as well, and is not limited to only the embodiment illustrated in FIG. 19.

FIG. 20 illustrates a paddle head 186' of a combination transvaginal probe 180' that includes imaging transducer 182 and a HIFU transducer 184a. Both imaging transducer 182 and HIFU transducer 184a comprise 1D phased array elements oriented so that the respective imaging and therapeutic ultrasound signals can be steered and focused in substantially the same plane, i.e., in a plane aligned with a longitudinal axis of the combination transvaginal probe. The 1D phased array elements of HIFU transducer 184a are generally semi-circular is shape, due to its slightly concave configuration.

In FIG. 21, a paddle head 192 of a combination transvaginal probe 194 is illustrated. Paddle head 192 includes a two-dimensional (2D) phased array imaging transducer 196 and a 2D phased array HIFU transducer 198. The 2D phased array elements of both the imaging transducer and HIFU transducer can thus be electronically steered and focused within a substantial conical volume, providing the clinician the capability to electronically control the location of the target area that is imaged and the location of the treatment site to which the HIFU waves are administered.

Mice Study

A laboratory study has shown that uterine fibroid tumors in a mouse can be treated completely, achieving nearly 100% shrinkage, using HIFU therapy. An Abstract of a paper submitted to the American Journal of Obstetrics and Gynecology to describe this study is included below, with minor modifications.

The objective of the study was to investigate the potential efficacy of high intensity focused ultrasound (HIFU) for the treatment of uterine fibroid tumors. A total of 60 female athymic nude mice were inoculated subcutaneously with $3-5\times10^6$ ELT-3 cells, a uterine fibroid tumor cell line. Tumor development was monitored using subcutaneous caliper measurements of the tumors. The HIFU probe was a concave, single-element high-power transducer, operating at a frequency of 3.5 MHz, and an intensity of 2000 WM/cm$^2$. The HIFU treatment consisted of scanning the tumors for 30-60 seconds, based on the tumor size. A single HIFU-treatment resulted in a tumor reduction of 91% within one month of the treatment. Histological analysis of HIFU-treated tumors showed coagulation necrosis, and nuclear fragmentation of tumor cells. It is thus concluded that the HIFU effectively reduced uterine fibroid tumor size in a nude mouse model. Further studies are needed to assess the in-situ response of uterine fibroids to HIFU treatment.

This study presents an important result; uterine fibroids can be treated at least twice to achieve a desired tumor shrinkage percentage. Several treatments could provide an optimal outcome for the patient. Such method may be valuable for large tumors that may not shrink to a desired volume, with a single treatment.

EKER Rat Study

Another study has shown that HIFU therapy can cause shrinkage of uterine fibroid tumors in a rat model (EKER rats). This study was conducted on an in-situ model of the uterine fibroid. Sham-treated animals did not show any tumor shrinkage. Instead, their tumors grew to about 85 times the volume at the time of treatment. In contrast, HIFU-treated animals showed tumor shrinkage of about 80% (20% of the volume at the time of treatment, after 3 months). Of particular interest in the results obtained in this study is the response of individual animals to the treatment. When tumors were completely treated, shrinkage was not optimal, perhaps due to fibrosis of the necrotic tumor instead of the absorption by the body. It should be noted that a histological analysis has not been performed yet to provide a definitive conclusion. When tumors were incompletely treated, especially when areas of viable tumor existed around the HIFU lesion, shrinkage was optimal, with minimal fibrosis.

This study presents an important result; an effective tumor de-bulking with significant shrinkage may be provided by HIFU-treatment procedures that create scattered lesions in the tumor, to allow body's macrophage absorption of the necrosis area, without fibrosis. This procedure may be combined with the above procedure of multiple treatments to achieve complete shrinkage and/or optimal de-bulking to a desired volume.

Cytokine Study

Also investigated was the inflammatory response of the body to HIFU treatment, and its possible effect on tumor necrosis. A host of cytokines (non-antibody proteins, released by macrophages (actively phagocytic cells), on contact with a specific antigen and which act as intercellular mediators, as in the generation of immune response) are known to be involved in such inflammatory response. It has been shown that therapeutic ultrasound has a stimulatory effect on the production of cytokines. The cytokine production is a signaling mechanism that results in attraction of more macrophages, and an enhanced immune response.

This study presents an important implication. The inflammatory response of the body to HIFU treatment may provide an enhanced rate of tumor shrinkage due to enhanced cytokine production. This mechanism may provide grounds for a treatment procedure that involves the production of scattered HIFU lesions in the uterine fibroid tumor, and obtaining an optimal tumor shrinkage due to enhanced immune response.

Synergistic Treatment

Synergistic effects of therapeutic ultrasound and anti-tumor compounds may provide a mechanism for treatment for uterine fibroids, involving a combination therapy using both anti-tumor drugs and HIFU. This management has two possibilities, including the use HIFU with the drugs currently available for uterine fibroids (GnRH agonists). These drugs can shrink the fibroids temporarily. As soon they are discontinued, the fibroids grow back to their original size. Since these drugs have side effects, they are primarily used for shrinking the fibroids before a myomectomy (surgical removal of the fibroids). HIFU treatment may be performed at the time when maximal shrinkage of the tumors due to drugs has occurred, thereby fixing the tumor size and preventing tumor re-growth. The second possibility is to use HIFU with the new anti-tumor compounds which may offer further advantages.

Methods of Administering the HIFU Therapy

Several methods for administering HIFU therapy of uterine fibroids are envisioned. These include the treatment of the entire tumor in a single procedure. It has been observed that a complete tumor treatment (100% shrinkage) may be obtained using this method. Alternatively, the tumor may be treated in several sessions, with sufficient time between each session for the macrophages in the patient's body to clear away the necrotic tissue resulting from the previous treatment session, effectively debriding the treatment side and exposing remaining tumor tissue for the next HIFU therapy session. In each session, a remaining part of the tumor is treated. A complete tumor treatment (100% shrinkage) in all of the tumors treated using this method has been observed. Scattered HIFU lesions in a tumor may also provide an optimal shrinkage, with minimal fibrosis. Several HIFU therapy sessions may be needed to completely eradicate the tumor. Further, as noted above, the treatment of a tumor using a combination of HIFU and drugs may yield synergistic results, particularly by beginning the HIFU therapy when the maximum benefit of the drug therapy on the tumor has been realized.

Use of Contrast Agents to Enhance HIFU Treatment

Ultrasound contrast agents provide an effective adjuvant tool for medical procedures involving both ultrasound diagnosis and therapy. Contrast agents can be employed to enhance HIFU therapy in four different ways. First, contrast agents can be used before therapy is initiated to improve the imaging procedure used to locate particular vascular structures for treatment. Second, contrast agents can be used to determine the focal point of a HIFU therapy transducer while the HIFU therapy transducer is operated at a relatively low power level, so that damage to normal tissue does not occur until the HIFU is transducer has been properly focused at the target location (such as a tumor) where tissue damage is desired, and the power level then increased. Third, contrast agents can improve the efficacy of the therapeutic dose of HIFU energy delivered, through a positive feedback mechanism that reduces the amount of HIFU energy required to damage tissue compared to that required when contrast agents are not present. Finally, when properly disposed, contrast agents can be used to shield adjacent or underlying non-target tissue from damage. This shielding effect occurs when sufficient quantities of contrast agents are administered to block the propagation of HIFU waves into the non-target tissue. Of course, various combinations of two or more of these techniques can also be employed in a single therapeutic implementation.

Before discussing the use of contrast agents in detail, it will be helpful to discuss the types of contrast agents that can be employed. Micro-bubbles serve as contrast agents for use with ultrasound, and contrast agents that readily form micro-bubbles when exposed to ultrasound energy are therefore preferred. Gas-filled contrast agents provide a large scattering cross section due to the significant difference between the compressibility of the contrast agent content (air or other gases) and the ambient surroundings of the contrast agent in the body (generally body fluids or tissue). Therefore, the interaction of ultrasound waves and a contrast agent leads to strong echo signals, resulting in enhanced hyperechogenecity of a region in the body where the contrast agent is disposed. It should be understood that contrast agents can be provided either as a liquid solution that already includes micro-bubbles when introduced into a patient's body, or as a liquid that can be induced to form micro-bubbles at a target location in a patient's body.

Many different prepared micro-bubbles solutions are commercially available for use as ultrasound contrast agents, including ECHOVIST™ (produced by Schering, Germany), ALBUNEXTM™ (Molecular Biosystems/Mallinckrodt, USA), SONAZOID™ (Amersham Health, Oslo, Norway), and OPTISON™ (Mallinckrodt, St Louis, Mo.). Generally, such ultrasound contrast agent preparations comprise suspensions of millions of tiny air- or gas-filled bubbles, with sizes as small as 1-10 µm. These micro-bubbles are stabilized within a biodegradable shell. Without this shell, the bubbles would be stable only transitorily (for only a few seconds), as the un-stabilized bubbles would soon merge into larger bubbles. Besides being potentially hazardous to the patient, large bubbles have different, and less suitable, reflective properties, that are not desirable in a contrast agent.

Liquids that can be used to generate micro-bubbles in-vivo include anesthetic agents, or other blood soluble agents having a relatively high vapor pressure. Such agents will readily vaporize when exposed to the slight elevated temperatures caused by low power ultrasound on tissue. Ultrasound waves can also induce cavitation in liquids, providing another mechanism for bubble formation. Because such bubbles are formed in-vivo at the target site, the more transitory nature of micro-bubbles lacking stabilizing shells is not a particular disadvantage, because the bubbles will exist at the imaging site long enough for their presence to have the desired effect. Halothane, isoflurane, and enflurane (fluorinated solvents) are exemplary of high vapor pressure aesthetics, whereas methoxyflurane is exemplary of a less volatile anesthetic. It should be understood that the high vapor pressure liquid does not necessarily need to be an anesthetic. Instead, high vapor pressure anesthetics represent known materials that are regularly used in-vivo and are substances whose toxicological effects are well understood. Many other high vapor pressure liquids are known and can be beneficially employed as ultrasound contrast agents, so long as the toxicological effects of such liquids are well understood and do not pose a health risk to the patient.

Two mechanisms can be used to induce in-vivo micro-bubble formation in suitable volatile liquids. Ultrasound energy can be used to slightly heat adjacent tissue, so that the heated tissue in turn heats the volatile liquid, which volatilizes and produces the micro-bubbles. If the adjacent tissue is not tissue that is to be heated in the course of administering HIFU therapy, care must be exercised such that the tissue is not heated to a temperature that damages the tissue or causes necrosis. Ultrasound energy can also be absorbed by certain volatile liquids directly. If sufficient ultrasound energy is delivered to a liquid, a phenomenon referred to as cavitation occurs. Cavitation is the formation, growth, and collapse of micro bubbles. The amount of energy that is required to induce cavitation is based on the strength of the attractive forces between the molecules that comprise the liquid. The implosion of these tiny bubbles is sufficiently energetic to provide at least some of the energy required to induce further cavitation. Because cavitation is such an energetic phenomenon, care must be exercised to avoid undesirable tissue damage. The cavitation phenomenon is a function of environmental characteristics (the temperature and pressure of the liquid) as well as physical properties of the liquid itself (surface tension, the attractive forces holding the components of the liquid together, etc.). Empirical studies based on specific volatile liquids and ultrasound power levels, preferably using animal models, should be conducted prior to inducing in-vivo micro-bubbles via cavitation to enhance ultrasound therapy. In general, less energetic ultrasound imaging waves will be less efficient in forming micro bubbles, because lower energy ultrasound imaging waves do not cause a sufficient temperature increase to occur. Preferably, the step of inducing volatile liquids to generate micro bubbles in-vivo will be achieved using HIFU, while simultaneously scanning the target area using conventional imaging ultrasound.

Returning now to the different ways in which ultrasound contrast agents can be employed, as noted above, ultrasound contrast agents can be used before HIFU-based therapy is initiated to locate particular vascular structures for treatment. The change in echogenicity provided by blood soluble ultrasound contrast agents (or ultrasound contrast agents that can be entrained in blood) can be used to differentiate high blood flow regions from low blood flow regions. Because tumors usually exhibit a blood flow pattern that is different than that of surrounding normal tissue, ultrasound contrast agents can enhance the visualization of tumors, thereby facilitating the identification of the target area for HIFU therapy. Furthermore, when initially administered, ultrasound contrast agents will be first carried through larger blood vessels (arteries, arterioles, veins, etc.) as opposed to capillaries. Thus, different vascular structures can be identified as potential targets for HIFU therapy. For example, a tumor can be treated by using ultrasound contrast agents to identify the major vascular structures providing blood flow to the tumor, and once identified, those structures can be destroyed using HIFU. As a result of destroying the vasculature structure(s) associated with a tumor, the tumor tissue is denied nutrients and oxygen that were previously conveyed by blood flowing through the vasculature structure(s) and eventually dies.

Also, by observing the movement of ultrasound contrast agents throughout vascular structures (using imaging ultrasound), damaged areas in the vascular tree can readily be identified. Bleeding from a damaged or injured blood vessel into a body cavity can lead to differential hyperechogenecity of the pooled blood in the leakage cavity, enabling the identification of the bleeding vessel. HIFU therapy can then be administered to the injury site on the blood vessel to stop the bleeding. Stabilized micro-bubbles are particularly useful for imaging a vascular structure, because tracking movement of the contrast agent throughout the vascular structure may require relatively longer bubble lifetimes.

The second use of ultrasound contrast agents in conjunction with HIFU therapy noted above was for identifying the location for targeting the focal point of the HIFU beam. The energy delivered at the focal point of a HIFU beam can damage tissue, by increasing its temperature sufficiently and can cause tissue necrosis. If the focal point of the HIFU beam is not properly directed, damage to non-target tissue in a patient's body can occur. As discussed in detail above, one technique to determine the focal point of the HIFU beam is to energize the HIFU transducer at a relatively low power, such that some thermal energy is imparted to the tissue at the focal point of the HIFU beam, but the amount of thermal energy delivered to the non-target tissue is insufficient to cause damage or tissue necrosis. Administering HIFU to tissue at energy levels too low to cause damage still changes the echogenicity of the tissue sufficiently to cause the focal point of the HIFU beam to appear as a bright spot in an image formed using ultrasound imaging waves. While one explanation for this effect is that a change in the temperature of the tissue causes a change in echogenicity, it is also believed that a more significant factor in producing the change in echogenicity is the interaction of the pressure oscillations of the low intensity HIFU ultrasound beam within the tissue, which causes microbubbles to form in the tissue. This technique can be modified, so that ultrasound contrast agents are first delivered to the target area. Volatile liquids work particularly well in this application. When volatile liquid contrast agents are present in the target area, the HIFU transducer is energized at an even lower power level (than when a contrast agent is not used). The contrast agent volatilizes to form micro bubbles, which are readily detectable using ultrasound imaging waves. Less energy is required to cause the contrast agent to form bubbles than is required to increase the temperature of tissue sufficiently to produce a detectable change in the echogenicity of the tissue (or to produce micro-bubbles in tissue that also produces a detectable change in the echogenicity of the tissue). The bubbles generated by the contrast agent will produce a substantially brighter spot in the ultrasound image than can be achieved when targeting tissue without the use of a contrast agent, and at an even lower energy level. Reduction of the HIFU energy used to determine the correct focal point position of the HIFU transducer to an even lower level than would be used without the contrast agent also ensures that the focal point of the HIFU transducer is evident in the ultrasound image produced by the imaging transducer, but without risk of damage to tissue that is not to be treated.

The third use for ultrasound contrast agents to enhance HIFU therapy provides enhanced heating, i.e., the contrast agent causes a positive feedback process to occur as a result of the resonance of the micro bubbles that enables a less energetic HIFU beam to achieve the same therapeutic dose that would be provided from a more energetic HIFU beam, if the contrast agent were not used. As noted above, volatile liquid ultrasound contrast agents respond to certain ultrasound frequencies by absorbing ultrasound energy and cavitating, thereby generating heat that raises the temperature of the surrounding tissue and liquid. This temperature increase reduces the amount of energy required to induce further cavitation. Thus, for the same energy input from an ultrasound beam, more micro bubbles are formed by cavitation, and the rate of micro bubble formation over time increases. Increasing the temperature of the liquid increases the amount of liquid that volatilizes, producing even more bubbles. This enhanced heating is a significant advantage when contrast agents are disposed in the focal region of a HIFU beam. The positive feedback process can result in highly efficient conversion of the acoustic energy to heat and reduces the HIFU energy required to heat targeted tissue sufficiently so that tissue damage and necrosis occur.

FIGS. 23A and 23B schematically illustrate a HIFU therapy probe 240 being used to induce cavitation to enhance HIFU therapy. Preferably probe 240 includes an imaging transducer and a therapy transducer 242, like the combined probes discussed in detail above. Of course, separate imaging and HIFU probes can alternatively be used, or probe 240 might then include only therapy transducer 242. In FIG. 23A, the focal point of therapy transducer 242 is directed to a treatment site 246a, which is within a fluid volume 244a. Fluid volume 244a includes a quantity of ultrasound contrast agent, such as one of the volatile liquids discussed above. It should be understood that fluid volume 244a can be either naturally occurring or artificial introduced. When therapy transducer 242 is energized at a level sufficient to produce ultrasound energy exceeding the cavitation threshold of the fluid in fluid volume 244a, cavitation is induced in the liquid in the fluid volume. The feedback process discussed above results in an efficient conversion of acoustic energy to thermal energy. Continued application of HIFU therapy will result in an increased temperature of the liquid in the fluid volume and adjacent tissue, resulting in therapeutic changes to tissue immediately adjacent to fluid volume 244a, such as a peripheral portion 250 of tumor 248a. It should be noted that the increased temperatures will affect all tissue adjacent to fluid volume 244a. It may be that such tissue will include non-target tissue.

FIG. 23B illustrates a fluid volume 244b that is surrounded by target tissue, so that the increased temperatures within a fluid volume 244b does not propagate to non-target tissue. Fluid volume 244b is disposed completely within a tumor 248b, and the focal point of therapy transducer 242 corresponds to a treatment site 246b within fluid volume 244b. While fluid volume 244b might be naturally occurring, as illustrated, a liquid-filled syringe 252 (including an ultrasound contrast agent) and a needle 254 have been used to artificially create fluid volume 244b. For example, the vascular system of tumor 248b can be mapped as described above, and the syringe and needle can be used to introduce a contrast agent into the tumor at a position disposed adjacent to a major blood vessel in the tumor. The HIFU therapy subsequently administered results in cavitation within fluid volume 244b, and the concomitant increased temperature causes tissue necrosis in the adjacent blood vessel, thereby depriving the tumor of blood flow (and of the nutrients and oxygen that are conveyed by the blood flow). With respect to FIG. 23A and FIG. 23B, it will be understood that the target tissue need not be a tumor, and that the target tissue could correspond to other types of tissue requiring HIFU therapy. It should also be understood that depending on the location of the target area, a syringe and needle may not be suitable to administer the liquid and contrast agent, and a catheter or other fluid delivery device might instead be employed for this function.

Yet another way in which ultrasound contrast agents can be used to enhance HIFU therapy is to shield non-target tissue from damage caused by the HIFU energy beam. This shielding effect occurs when a sufficient quantity of contrast agent blocks the propagation of HIFU waves to the non-target tissue, which may underlie the contrast agent. Since contrast agents reflect ultrasound waves more strongly than tissue does, the reflection of ultrasound energy can be used not only to enhance images of a treatment site, but also to prevent undesired tissue damage to tissue disposed beyond the contrast agent, since the HIFU ultrasound beam is reflected before it encounters such tissue. This shielding mechanism enables differential treatment of a certain region of a tumor or abnormal tissue, while sparing the regions beyond the contrast agent. Of course, the physical structure of the area being treated will determine the effectiveness of such shielding. There must be a fluid cavity or volume, natural to the anatomy or artificial, proximate the tissue to be protected and disposed between the tissue to be protected and the focal point of the HIFU beam, so that the contrast agents can be introduced into the cavity or volume.

There are many medical techniques that can be employed to generate an artificial volume if a natural fluid vessel or cavity is not present where needed to contain a contrast agent that will shield non-target tissue from being damaged a HIFU beam. Much of the body's tissue is sufficiently resilient so that small volumes of liquid and contrast agent can readily be created therein. One technique is to introduce a fluid using a catheter, or a syringe and needle. As the fluid is forced into the tissue, the tissue will either slightly compress or shift so as to define a volume to accommodate the liquid being introduced. Either a solution of micro bubbles or a volatile liquid that will generate micro-bubbles when adjacent tissue is treated with HIFU can thus be infused into tissue to generate an artificial fluid pocket. Those of ordinary skill in the art will recognize that many other known techniques might be used to introduce a contrast agent to shield non-target tissue from a therapeutic HIFU beam, as described above.

If a volatile liquid contrast agent is employed, and cavitation of that volatile liquid is induced, then some thermal damage to tissue that the HIFU beam does not reach (because of the shielding effect of the contrast agent) may still occur, simply because of the thermal effects of the cavitation. If a prepared solution of stabilized micro bubbles is employed as a contrast agent, cavitation is less likely (the prepared solutions are generally less volatile, and have a higher cavitation threshold), and tissue blocked by the contrast agent from receiving the HIFU beam is less likely to suffer thermal damage. Of course, the closer the focal point of the HIFU beam is to the contrast agent solution, and the more energetic the HIFU beam, the more energy will be absorbed by the contrast agent solution. At some point, the contrast agent solution will be heated to the point that some thermal damage to tissue beyond the contrast agent shield may occur—not because the HIFU beam reached that tissue, but because the HIFU beam raised the temperature of the contrast agent sufficiently to damage tissue proximate the contrast agent.

FIGS. 24A and 24B schematically illustrate a HIFU therapy probe 240 being used to apply HIFU therapy to a treatment site while an ultrasound contrast agent disposed adjacent to the treatment site blocks the HIFU beam from propagating beyond the treatment site into non-target tissue. As noted above, probe 240 can include an imaging transducer along with therapy transducer 242. In FIG. 24A, the focal point of therapy transducer 242 is directed to a treatment site 246c, which is disposed within a tumor 248c. Treatment site 246c is disposed proximate a periphery of tumor 248c, and it is likely that the HIFU beam may undesirably propagate beyond treatment site 246c, into non-target tissue disposed outside of tumor 248c. To prevent such propagation from occurring, an ultrasound contrast agent is introduced into a fluid volume 244c (a natural or artificial volume), which is disposed outside tumor 248c and within the propagation path of the HIFU beam. Fluid volume 244c is thus beyond treatment site 246c (relative to therapy transducer 242) so that the contrast agent in fluid volume 244c does not prevent the HIFU beam from reaching treatment site 246c, but does block the HIFU beam from undesirably affecting tissue in a region 260a.

Referring now to FIG. 24B, a quantity of ultrasound contrast agent has been introduced into a fluid volume 244d, which is disposed within a tumor 248d. Again, fluid volume 244d can be naturally occurring; however, creating an artificial volume within tumor 248d enables a clinician greater control in positioning the volume to shield specific portions of tissue. When therapy transducer 242 is energized at a level sufficient to provide the desired HIFU therapy at treatment site 246d, the ultrasound contrast agent in fluid volume 244d acts a shield to prevent the HIFU beam from propagating into tissue 260b. While FIG. 23B indicates that the treatment site is within a tumor, it should be understood the same approach applies equally to the treatment of other structures, such as an organ, enabling selective targeting of tissue to be therapeutically treated, while shielding tissue that is not.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for using an ultrasound contrast agent to enhance administration of a high intensity focused ultrasound (HIFU) therapy to a specific treatment site within a target area with a therapeutic ultrasonic transducer, comprising the steps of:
   (a) introducing a contrast agent to the target area, the contrast agent having a characteristic of altering reflection characteristics of an ultrasonic wave; and
   (b) using the contrast agent to enhance the administration of the HIFU therapy in at least one of the following manners:
      (i) enabling a focal point of the therapeutic ultrasonic transducer to be visualized in an image generated when the therapeutic ultrasonic transducer is energized at a power level insufficient to damage tissue, the focal point being readily visually identifiable in the image due to a change in the reflection characteristics of an ultrasonic wave produced by the therapeutic ultrasonic transducer caused by the contrast agent, thereby enabling the focal point of the therapeutic ultrasonic transducer to be targeted at the treatment site, and not at non-target tissue; and
      (ii) directing a focal point of the therapeutic ultrasonic transducer at the specific treatment site, such that a fluid filled volume containing the contrast agent is disposed distal to the specific treatment site, the contrast agent being administered in sufficient quantity so as to act as a shield to prevent tissue disposed distal to the specific treatment site from being adversely affected by the HIFU therapy administered to the specific treatment site.

2. The method of claim 1, wherein the step of directing a focal point of the therapeutic ultrasonic transducer at a fluid filled volume containing the contrast agent, the contrast agent acting as a shield to prevent tissue not disposed at the specific treatment site from being adversely affected by the HIFU therapy administered to the specific treatment site comprises the step of directing the focal point of the therapeutic ultrasonic transducer such that a first distance separating the fluid filled volume from the therapeutic ultrasonic transducer is greater than a second distance separating the treatment site from the therapeutic ultrasonic transducer.

3. The method of claim 1, wherein when the contrast agent is to be used as a shield to protect non-target tissue from damage to enhance therapeutic application of HIFU, the step of introducing a contrast agent to the target area comprises the steps of determining which portions of the target area the contrast agent needs to be disposed in to protect non-target tissue, and introducing the contrast agent into the portions so determined.

4. The method of claim 3, wherein if no fluid volume is disposed in a portion of the target area where the contrast agent needs to be disposed to be used as a shield to protect non-target tissue from damage, further comprising the step of introducing the contrast agent into tissue corresponding to that portion.

5. The method of claim 3, wherein if no fluid volume is disposed in a portion of the target area where the contrast agent needs to be disposed to be used as a shield to protect non-target tissue from damage, further comprising the steps of creating a void in that portion of the target area, and introducing the contrast agent into the void created.

6. The method of claim 1, wherein the step of using the contrast agent to enhance a therapeutic application of HIFU in at least one of the following manners further comprises the step of using the contrast agent to enhance a therapeutic application of HIFU in each of the manners identified in claim 1.

7. A method for using an ultrasound contrast agent to enhance administration of a high intensity focused ultrasound (HIFU) therapy to a specific treatment site within a target area, comprising the steps of:
  (a) introducing a contrast agent into the target area, the contrast agent having a characteristic of altering reflection characteristics of an ultrasonic wave;
  (b) positioning a scanning ultrasonic transducer and a therapeutic ultrasonic transducer generally adjacent to the target area;
  (c) energizing the scanning ultrasonic transducer to produce an image of the target area;
  (d) displaying the image of the target area;
  (e) energizing the therapeutic ultrasonic transducer to produce ultrasonic waves generally directed toward the treatment site, but at a power level insufficient to adversely affect tissue;
  (f) identifying a focal point of the therapeutic ultrasonic transducer in the image of the target area that is displayed, the focal point being readily identifiable due to a change in the reflection characteristics caused by the contrast agent; and
  (g) moving the therapeutic ultrasonic transducer until its focal point, which is visible in the image of the target area, is directed at the treatment site.

8. The method of claim 7, further comprising the step of increasing the power level of the therapeutic ultrasonic transducer to a level sufficient to induce a therapeutic effect, to produce pulses of therapeutic waves of the HIFU energetic enough to induce a therapeutic effect at the treatment site.

9. The method of claim 7, wherein the step of energizing the therapeutic ultrasonic transducer to produce therapeutic waves comprises the step of producing pulses of the therapeutic waves, and further comprising the steps of:
  (a) synchronizing the pulses of therapeutic waves produced by the therapeutic ultrasonic transducer relative to the imaging waves produced by the scanning ultrasonic transducer, such that noise in the imaging data arising from the therapeutic waves is displayed in a specific portion of the displayed target area; and
  (b) enabling a user to shift the noise arising from the therapeutic waves that is displayed in the specific portion of the displayed target area to a different portion of the displayed target area, so that the noise arising from the therapeutic waves can be moved to a portion of the displayed target area that does not correspond to the treatment site, thereby enabling the treatment site to be observed in real time as the pulses of therapeutic waves of the HIFU are administered to the treatment site.

10. The method of claim 9, further comprising the step of increasing the power level of the therapeutic ultrasonic transducer to a level sufficient to induce a therapeutic effect, to produce pulses of therapeutic waves of the HIFU energetic enough to induce a therapeutic effect at the treatment site.

11. The method of claim 9, further comprising the step of enabling a user to adjust a duration of each pulse of therapeutic waves, to ensure that the duration of each pulse of therapeutic waves is not so great as to overwhelm the imaging data used to generate the visual representation.

12. The method of claim 7, wherein the step of introducing a contrast agent to the target area comprises the step of introducing a blood soluble contrast agent into a patient's blood stream.

13. The method of claim 7, wherein the contrast agent comprises a volatile liquid that vaporizes in response to heat levels that are insufficient to damage biological tissue, thus forming bubbles that alter the reflection characteristics of ultrasonic waves used to produce the imaging data.

14. The method of claim 13, wherein the step of moving the therapeutic ultrasonic transducer comprises the step of moving the therapeutic ultrasonic transducer such that the treatment site selected is a fluid filled volume disposed adjacent to tissue to be treated, the contrast agent being disposed in the fluid filled volume, and further comprising the step of increasing the power level of the therapeutic ultrasonic transducer to a level sufficient to induce cavitation in the contrast agent disposed at the treatment site, such cavitation resulting in a feedback mechanism that increases an efficiency with which the therapeutic waves of the HIFU are transformed into heat, such heat inducing a therapeutic change in the tissue to be treated.

15. The method of claim 13, wherein the contrast agent comprises an anesthetic agent.

16. The method of claim 7, wherein before the step of energizing the therapeutic ultrasonic transducer at a power level insufficient to induce a therapeutic effect, further comprising the step of selecting the specific treatment site to apply HIFU therapy to, based on portions of the displayed target area that are readily identifiable due to the contrast agent's altering the reflection characteristics of the ultrasonic scanning waves.

17. The method of claim 16, wherein the step of selecting the specific treatment site to apply HIFU therapy to comprises the step of observing the displayed target area to monitor a movement of the contrast agent through a vascular system associated with the target area, and selecting a desired portion of the vascular system associated with the target area as the treatment site.

18. The method of claim 7, wherein the step of moving the therapeutic ultrasonic transducer comprises the step of moving the therapeutic ultrasonic transducer such that a fluid filled volume containing a quantity of the contrast agent is disposed adjacent to the treatment site, a first distance separating the fluid filled volume from the therapeutic ultrasonic transducer being greater than a second distance separating the treatment site from the therapeutic ultrasonic transducer, the contrast agent in the fluid filled volume acting as a shield to prevent non-target tissue from being treated by the therapeutic waves of the HIFU when the therapeutic ultrasonic transducer is energized at a level sufficient to induce therapy at the treatment site.

19. The method of claim 7, wherein if the contrast agent is to be used as a shield to protect non-target tissue from damage to enhance the therapeutic application of HIFU, the step of introducing a contrast agent to the target area comprises the steps of determining which portions of the target area the contrast agent needs to be disposed in to protect non-target tissue, and introducing the contrast agent into the portions so determined.

20. The method of claim 19, wherein if no fluid volume is disposed in a portion of the target area in which the contrast agent is required to be disposed to be used as a shield to protect non-target tissue from damage, further comprising the step of injecting the contrast agent into tissue corresponding to that portion.

21. The method of claim 19, wherein if no fluid volume is disposed in a portion of the target area in which the contrast agent is required to be disposed to be used as a shield to protect non-target tissue from damage, further comprising the steps of creating a void in that portion of the target area, and introducing the contrast agent into the void created.

22. A method for using a contrast agent to both enhance the ultrasound imaging of a target area and to facilitate providing a focused ultrasound therapy to a specific treatment site disposed within the target area, comprising the steps of:
   (a) introducing a contrast agent into the target area, the contrast agent altering reflection characteristics of an ultrasonic wave;
   (b) positioning a scanning ultrasonic transducer and a therapeutic ultrasonic transducer generally adjacent to the specific treatment site;
   (c) energizing the scanning ultrasonic transducer to scan the target area, producing an image of the target area;
   (d) displaying the image of the target area;
   (e) energizing the therapeutic ultrasonic transducer at a reduced power level to produce a high intensity focused ultrasound (HIFU) beam, generally directed toward the treatment site, but at an energy insufficient to adversely affect tissue in the target area;
   (f) observing a visual representation of a focal point of the HIFU beam in the image, the focal point being readily visible in the image due to a change in reflection characteristics caused by the contrast agent;
   (g) positioning the therapeutic ultrasonic transducer as required until the focal point displayed in the image of the target area is directed at the treatment site; and
   (h) energizing the therapeutic ultrasonic transducer at a greater power level sufficient to administer the focused ultrasound therapy directly to the treatment site.

23. The method of claim 22, wherein the step of energizing the therapeutic ultrasonic transducer at a greater power level sufficient to administer the focused ultrasound therapy to the treatment site comprises the step of producing pulses of the therapeutic waves.

24. The method of claim 22, further comprising the steps of:
   (a) synchronizing the pulses of therapeutic waves produced by the therapeutic ultrasonic transducer relative to the imaging waves produced by the scanning ultrasonic transducer, such that noise in the imaging data arising from the therapeutic waves is displayed in a specific portion of the displayed target area; and
   (b) enabling a user to shift the noise arising from the therapeutic waves that is displayed in the specific portion of the displayed target area to a different portion of the displayed target area, so that the noise arising from the therapeutic waves can be moved to a portion of the displayed target area that does not correspond to the treatment site, thereby enabling the treatment site to be observed in real time as the pulses of therapeutic waves of the HIFU are administered to the treatment site.

25. The method of claim 22, wherein:
   (a) the contrast agent comprises a volatile liquid that vaporizes in response to heat levels that are insufficient to damage biological tissue, thus forming bubbles that alter the echogenicity of the therapeutic waves of the HIFU;
   (b) the step of positioning the therapeutic ultrasonic transducer comprises the step of positioning the therapeutic ultrasonic transducer such that the treatment site selected is a fluid filled volume including the contrast agent disposed adjacent to tissue to be treated; and
   (c) the step of energizing the therapeutic ultrasonic transducer at a greater power level comprises the step of energizing the therapeutic ultrasonic transducer at a power level sufficient to induce cavitation in the contrast agent disposed in the fluid filled volume, such cavitation resulting in a feedback mechanism that increases an efficiency with which the therapeutic waves of the HIFU are transformed into heat, such heat inducing a therapeutic change in the tissue to be treated.

26. The method of claim 22, wherein the step of positioning the therapeutic ultrasonic transducer comprises the step of positioning the therapeutic ultrasonic transducer such that the treatment site selected is adjacent to a fluid filled volume containing a quantity of the contrast agent, the contrast agent in the fluid filled volume acting as a shield to prevent non-target tissue from being treated by the therapeutic waves of the HIFU.

27. The method of claim 22, wherein before the step of energizing the therapeutic ultrasonic transducer at a reduced power level to produce a high intensity focused ultrasound (HIFU) beam, further comprising the step of selecting the specific treatment site to which HIFU therapy is to be applied, based on portions of the displayed target area that are readily identifiable due to the contrast agent's altering the reflection characteristics of ultrasonic scanning waves generated by the scanning ultrasonic transducer.

28. The method of claim 27, wherein the step of selecting the specific treatment site comprises the step of observing the displayed target area to monitor a movement of the contrast agent through a vascular system associated with the target area, and selecting a desired portion of the vascular system associated with the target area as the treatment site.

29. A method for using an ultrasound contrast agent to enhance administration of a high intensity focused ultrasound (HIFU) therapy to a specific treatment site within a target area with a therapeutic ultrasonic transducer, comprising the steps of:
   (a) introducing a contrast agent to the target area, the contrast agent having a characteristic of altering reflection characteristics of an ultrasonic wave; and
   (b) using the contrast agent to enhance the administration of the HIFU therapy by directing a focal point of the therapeutic ultrasonic transducer at the specific treatment site, such that a fluid filled volume containing the contrast agent is disposed distal to the specific treatment site, the fluid filled volume being part of the target area, the contrast agent being administered in sufficient quantity so as to act as a shield to prevent tissue disposed distal to the specific treatment site from being adversely affected by the HIFU therapy administered to the specific treatment site.

30. A method for using an ultrasound contrast agent to enhance administration of a high intensity focused ultrasound (HIFU) therapy to a specific treatment site within a target area with a therapeutic ultrasonic transducer, comprising the steps of:

(a) administering a contrast agent in sufficient quantity between a HIFU transducer and non-target tissue distal of the specific treatment site such that the contrast agent will act as a shield to prevent the non-target tissue disposed distal of the specific treatment site from being adversely affected when HIFU therapy is administered to the specific treatment site, the contrast agent having a characteristic of altering reflection characteristics of an ultrasonic wave; and (b) administering HIFU therapy to the specific treatment site while the sufficient quantity of the contrast agent is disposed between the HIFU transducer and non-target tissue distal of the specific treatment, the sufficient quantity of contrast agent acting as a shield to prevent the non-target tissue disposed distal of the specific treatment site from being adversely affected by the HIFU therapy administered to the specific treatment site.

* * * * *